United States Patent
Demeule et al.

(10) Patent No.: US 8,710,013 B2
(45) Date of Patent: Apr. 29, 2014

(54) PHARMACEUTICAL COMPOSITIONS OF PACLITAXEL, PACLITAXEL ANALOGS OR PACLITAXEL CONJUGATES AND RELATED METHODS OF PREPARATION AND USE

(75) Inventors: Michel Demeule, Beaconsfield (CA); Christian Che, Longueuil (CA); Anthony Regina, Montréal (CA); Richard Béliveau, Montréal (CA); Catherine Gagnon, Montréal-Nord (CA); Jean-Paul Castaigne, Mont-Royal (CA); Reinhard Gabathuler, Verdun (CA)

(73) Assignee: Angiochem Inc., Montreal (CA)

( * ) Notice: Subject to any disclaimer, the term of this patent is extended or adjusted under 35 U.S.C. 154(b) by 389 days.

(21) Appl. No.: 12/988,269

(22) PCT Filed: Apr. 20, 2009

(86) PCT No.: PCT/CA2009/000542
§ 371 (c)(1),
(2), (4) Date: Jan. 7, 2011

(87) PCT Pub. No.: WO2009/127072
PCT Pub. Date: Oct. 22, 2009

(65) Prior Publication Data
US 2011/0112036 A1    May 12, 2011

Related U.S. Application Data

(60) Provisional application No. 61/124,677, filed on Apr. 18, 2008.

(51) Int. Cl.
*A61K 38/00* (2006.01)
*A61P 35/00* (2006.01)

(52) U.S. Cl.
USPC .............................. 514/19.3; 514/1.1

(58) Field of Classification Search
None
See application file for complete search history.

(56) References Cited

U.S. PATENT DOCUMENTS

| | | | |
|---|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A * | 7/1999 | Burchett et al. ............... 514/449 |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |
| 6,376,648 B2 | 4/2002 | White et al. |
| 6,391,305 B1 | 5/2002 | Feng et al. |
| 6,391,913 B1 * | 5/2002 | Page et al. ..................... 514/449 |
| 6,469,047 B1 | 10/2002 | Jackson et al. |
| 6,475,481 B2 | 11/2002 | Talmadge |
| 6,475,781 B1 | 11/2002 | Mercola et al. |

(Continued)

FOREIGN PATENT DOCUMENTS

CA      2283474        9/1998
CA      2525236 A1     1/2005

(Continued)

OTHER PUBLICATIONS

Ballabh et al., "The Blood-Brain Barrier: An Overview Structure, Regulation, and Clinical Implications," *Neurobiol Dis.* 16:1-13 (2004).
Bickel et al., "Delivery of Peptides and Proteins Through the Blood-Brain Barrier," *Adv Drug Deliv Rev.* 46:247-279 (2001).
Boado, "Blood-brain Barrier Transport of Non-viral Gene and RNAi Therapeutics," *Pharm Res.* 24:1772-1787 (2007).
Bork, "Powers and Pitfalls in Sequence Analysis: The 70% Hurdle," *Genome Res.* 10:398-400 (2000).
Bork et al., "Go Hunting in Sequence Databases But Watch Out for the Traps," *Trends Genet.* 12:425-427 (1996).

(Continued)

*Primary Examiner* — Marcela M Cordero Garcia
(74) *Attorney, Agent, or Firm* — Kristina Bieker-Brady; Clark & Elbing LLP

(57) ABSTRACT

Pharmaceutical compositions useful for hydrophobic agents paclitaxel, paclitaxel analogs and conjugates thereof (e g ANG1005) which do not contain Cremophor™ The compositions further comprise an optional tonicity agent, a buffering agent a bulking agent and a solubilizing agent which is not Cremophor™ Methods of preparing said compositions and of said compositions in the treatment of cancer are also included.

31 Claims, 3 Drawing Sheets

(56) References Cited

U.S. PATENT DOCUMENTS

| | | |
|---|---|---|
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 2003/0129186 A1 | 7/2003 | Beliveau et al. |
| 2003/0170891 A1 | 9/2003 | McSwiggen |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2004/0241174 A1* | 12/2004 | Amphlett et al. ......... 424/178.1 |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1* | 8/2006 | Beliveau et al. ................ 514/8 |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2009/0016959 A1 | 1/2009 | Beliveau et al. |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | |
|---|---|---|
| CA | 2637893 | 7/2007 |
| CA | 2638034 | 7/2007 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EP | 0393431 | 10/1990 |
| EP | 0495049 B1 | 7/1992 |
| EP | 1982699 A1 | 10/2008 |
| EP | 2333074 A1 | 6/2011 |
| JP | 2007-509977 A | 4/2007 |
| WO | WO 87/05702 | 9/1987 |
| WO | WO 96/31531 | 10/1996 |
| WO | WO 96/35788 | 11/1996 |
| WO | WO 96/39183 | 12/1996 |
| WO | WO 96/40210 | 12/1996 |
| WO | WO 97/33996 | 9/1997 |
| WO | WO 97/40854 | 11/1997 |
| WO | WO 00/01417 | 1/2000 |
| WO | WO 00/71574 | 11/2000 |
| WO | WO 01/30319 | 5/2001 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2010/043047 | 4/2010 |
| WO | WO 2010/043049 | 4/2010 |
| WO | WO 2010/063122 | 6/2010 |
| WO | WO 2010/063123 | 6/2010 |
| WO | WO 2010/063124 | 6/2010 |
| WO | WO 2010/069074 | 6/2010 |
| WO | WO 2010/121379 | 10/2010 |
| WO | WO 2010/142035 | 12/2010 |
| WO | WO 2011/000095 | 1/2011 |
| WO | WO-2011/008823 A2 | 1/2011 |
| WO | WO 2011/041897 | 4/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |

(56) References Cited

FOREIGN PATENT DOCUMENTS

| | | |
|---|---|---|
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/032591 A1 | 3/2013 |
| WO | WO-2013/049332 A1 | 4/2013 |
| WO | WO-2013/063468 A1 | 5/2013 |
| WO | WO-2013/071272 A1 | 5/2013 |
| WO | WO-2013/078564 A2 | 6/2013 |
| WO | WO-2013/120107 A1 | 8/2013 |
| WO | WO-2013/131032 A1 | 9/2013 |

OTHER PUBLICATIONS

Brenner, "Errors in Genome Annotation," *Trends Genet.* 15:132-133 (1999).
Castex et al., "2-Pyrrolinodoxorubicin and Its Peptide-vectorized Form Bypass Multidrug Resistance," *Anticancer Drugs.* 15:609-617 (2004).
Coon et al., "Solutol HS 15, Nontoxic Polyoxyethylene Esters of 12-hydroxystearic Acid, Reverses Multidrug Resistance," *Cancer Res.* 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," Bioconjug Chem. 16:1299-1309 (2005).
Dagenais et al., "Development of an In Situ Mouse Brain Perfusion Model and Its Application to mdr1a P-glycoprotein-deficient Mice," *J Cereb Blood Flow Metab.* 20:381-386 (2000).
Deane et al., "LRP/Amyloid β-Peptide Interaction Mediates Differential Brain Efflux of Aβ Isoforms," *Neuron.* 43:333-344 (2004).
Dehouck et al., "A New Function for the LDL Receptor: Transcytosis of LDL Across the Blood-Brain Barrier," *J Cell Biol.* 138:877-889 (1997).
Dehouck et al., "An Easier, Reproducible, and Mass-production Method to Study the Blood-brain Barrier in Vitro," *J Neurochem.* 54:1798-1801 (1990).
Dehouck et al., "Drug Transfer Across the Blood-Brain Barrier: Correlation Between In Vitro and In Vivo Models," *J Neurochem.* 58:1790-1797 (1992).
Demeule et al., "High Transcytosis of Melanotransferrin (P97) Across the Blood-Brain Barrier," *J Neurochem.* 83:924-933 (2002).
Demeule et al., "Identification and Design of Peptides As a New Drug Delivery System For the Brain," *J Pharmacol Exp Ther.* 324:1064-1072 (2008).
Demeule et al., "Isolation of Endothelial Cells from Brain, Lung, and Kidney: Expression of the Multidrug Resistance P-Glycoprotein Isoforms," *Biochem Biophys Res Commun.* 281:827-834 (2001).
Doerks et al., "Protein Annotation: Detective Work for Function Prediction," *Trends Genet.* 14:248-250 (1998).
Fillebeen et al., "Receptor-Mediated Transcytosis of Lactoferrin Through the Blood-Brain Barrier," *J Biol Chem.* 274:7011-7017 (1999).
Fromm, "P-glycoprotein: A Defense Mechanism Limiting Oral Bioavailability and CNS Accumulation of Drugs," *Int J Clin Pharmacol Ther.* 38:69-74 (2000).
Gelmon, "The Taxoids: Paclitaxel and Docetaxel," *Lancet.* 344:1267-1272 (1994).
Gewirtz, "A Critical Evaluation of the Mechanisms of Action Proposed For the Antitumor Effects of the Anthracycline Antibiotics Adriamycin and Daunorubicin," *Biochem Pharmacol.* 57:727-741 (1999).
Grabb et al., "Neoplastic and Pharmacological Influence on the Permeability of an in vitro Blood-Brain Barrier," *J Neurosurg.* 82:1053-1058 (1995).
Guillot et al., "Angiotensin Peptide Regulation of Bovine Brain Microvessel Endothelial Cell Monolayer Permeability," *J Cardiovasc Pharmacol.* 18:212-218 (1991).

Gumbleton et al., "Progress and Limitations in the Use of In Vitro Cell Cultures to Serve as a Permeability Screen for the Blood-Brain Barrier," *J Pharm Sci.* 90:1681-1698 (2001).
Hawkins et al., "The Blood-Brain Barrier/Neurovascular Unit in Health and Disease," *Pharmacol Rev.* 57:173-185 (2005).
Hussain et al., "The Mammalian Low-Density Lipoprotein Receptor Family," *Annu Rev Nutr.* 19:141-172 (1999).
Ito et al., "Functional Characterization of the Brain-to-Blood Efflux Clearance of Human Amyloid-β Peptide (1-40) Across the Rat Blood-Brain Barrier," *Neurosci Res.* 56:246-252 (2006).
Ke et al., "Gene Delivery Targeted to the Brain Using an Angiopep-conjugated Polyethyleneglycol-modified Polyamidoamine Dendrimer," *Biomaterials.* 30:6976-6985 (2009).
Kiernan, "Fluorescent-Labelled Aprotinin: A New Reagent for the Histochemical Detection of Acid Mucosubstances," *Histochemie.* 34: 77-84 (1973).
Kobayashi et al., "The Protease Inhibitor Bikunin, a Novel Anti-Metastatic Agent," *Biol Chem.* 384:749-754 (2003).
Koo et al., "Differential Expression of Amyloid Precursor Protein mRNAs in Cases of Alzheimer's Disease and in Aged Nonhuman Primates," *Neuron.* 2:97-104 (1990).
Kounnas et al, "LDL Receptor-related Protein, a Multifunctional ApoE Receptor, Binds Secreted Beta-amyloid Precursor Protein and Mediates Its Degradation," *Cell.* 82:331-340 (1995).
Koziara et al., "In Situ Blood-brain Barrier Transport of Nanoparticles," *Pharm Res.* 20:1772-1778 (2003).
Kreuter et al., "Apolipoprotein-Mediated Transport of Nanoparticle-Bound Drugs Across the Blood-Brain Barrier," *J Drug Target.* 10:317-325 (2002).
Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res.* 20:409-416 (2003).
Kreuter, "Nanoparticulate Carriers for Drug Delivery to the Brain," *Nanoparticles as Drug Carriers,* Torchilin VP, Imperial College Press, London pp. 527-547 (2006).
Laccabue et al., "A Novel Taxane Active against an Orthotopically Growing Human Glioma Xenograft," *Cancer.* 92:3085-3092 (2001).
Lai et al., "The Critical Component to Establish in vitro BBB Model: Pericyte," *Brain Res Rev.* 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler.* 366:743-748 (1985).
Larsson, "Megalin, an Endocytocic Receptor With Signalling Potential," *Acta Universitatis Upsaliensis Uppsala* 1-60 (2006).
Ma et al., "Cationic Charge-Dependent Hepatic Delivery of Amidated Serum Albumin," *J Control Release.* 102:583-594 (2005).
Marinò et al., "Megalin-Mediated Transcytosis of Thyroglobulin by Thyroid Cells is a Calmodulin-Dependent Process," *Thyroid.* 10:461-469 (2000).
Marinò et al., "Transcytosis of Retinol-Binding Protein Across Renal Proximal Tubule Cells After Megalin (gp 330)-Mediated Endocytosis," *J Am Soc Nephrol.* 12:637-648 (2001).
Martel et al., "Transport of Apolipoproteins E and J at the Blood-Brain Barrier Relevance to Alzheimer's disease," *S.T.P. Pharma Sciences.* 7:28-36 (1997).
Mazel et al., "Doxorubicin-peptide Conjugates Overcome Multidrug Resistance," *Anticancer Drugs.* 12:107-116 (2001).
McCarty, "Cell Biology of the Neurovascular Unit: Implications for Drug Delivery Across the Blood-Brain Barrier," *Assay Drug Dev Technol.* 3:89-95 (2005).
Moestrup et al., "Evidence that Epithelial Glycoprotein 330/Megalin Mediates Uptake of Polybasic Drugs," *J.Clin. Invest.* 96:1404-1413 (1995).
Moore et al., "The Role of Flexible Tethers in Multiple Ligand-receptor Bond Formation Between Curved Surfaces," *Biophys J.* 91:1675-1687 (2006).
Muratovska et al., "Conjugate for Efficient Delivery of Short Interfering RNA (siRNA) Into Mammalian Cells," *FEBS Lett.* 558:63-68 (2004).

(56) References Cited

OTHER PUBLICATIONS

Ngo et al., "Computational Complexity; Protein Structure Prediction, and the Levinthal Paradox," *The Protein Folding Problem and Tertiary Structure Prediction* Merz, Jr. and Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther.* 5:174-179 (2006).
Orlando et al., "Identification of the Second Cluster of Ligand-Binding Repeats in Megalin as a Site for Receptor-Ligand Interactions," *Proc Natl Acad Sci.* 94:2368-2373 (1997).
Pan et al., "Efficient Transfer of Receptor-Associated Protein (RAP) Across the Blood-Brain Barrier," *J Cell Sci.* 117:5071-5078 (2004).
Pardridge, "Blood-Brain Barrier Biology and Methodology," *J Neurovirol.* 5:556-569 (1999).
Pardridge, "CNS Drug Design Based on Principles of Blood-Brain Barrier Transport," *J Neurochem.* 70:1781-1792 (1998).
Pardridge, "Drug Targeting to The Brain," *Pharm Res.* 24:1733-1744 (2007).
Peri et al., "D-Glucose as a Regioselectively Addressable Scaffold for Combinatorial Chemistry on Solid Phase," *J Carbohydr Chem.* 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem.* 279:35037-35046 (2004).
Qu et al., "Carbohydrate-based Micelle Clusters Which Enhance Hydrophobic Drug Bioavailability by Up to 1 Order of Magnitude," *Biomacromolecules.* 7:3452-3459 (2006).
Ramakrishnan, "The Role of P-glycoprotein in the Blood-Brain Barrier," *Einstein Q J Biol Med.* 19:160-165 (2003).
Rawat et al., "Lipid Carriers: A Versatile Delivery Vehicle for Proteins and Peptides," *Yakugaku Zasshi.* 128:269-280 (2008).
Régina et al., "Antitumour Activity of ANG1005, a Conjugate Between Paclitaxel and the New Brain Delivery Vector Angiopep-2," *Br J Pharmacol.* 155:185-197 (2008).
Régina et al., "Differences in Multidrug Resistance Phenotype and Matrix Metalloproteinases Activity Between Endothelial Cells from Normal Brain and Glioma," *J Neurochem.* 84:316-324 (2003).
Scherrmann, "Drug Delivery to Brain Via the Blood-Brain Barrier," *Vascul Pharmacol.* 38:349-354 (2002).
Schinkel, "P-Glycoprotein, A Gatekeeper in the Blood-Brain Barrier," *Adv Drug Deliv Rev.* 36:179-194 (1999).
Seidel et al., "Effects of Trasylol on the Blood-Brain Barrier in Rats," *Naunyn Schmiedebergs Arch Pharmacol.* 284:R73 (1974).
Shibata et al., "Clearance of Alzheimer's Amyloid-$\beta_{1-40}$ Peptide From Brain by LDL Receptor-Related Protein-1 at the Blood-Brain Barrier," *J Clin Invest.* 106:1489-1499 (2000).
Shiiki et al., "Brain Insulin Impairs Amyloid-β(1-40) Clearance From the Brain," *J Neurosci.* 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther.* 258:459-465 (1991).
Skolnick et al., "From Genes to Protein Structure and Function: Novel Applications of Computational Approaches in the Genomic Era," *Trends Biotechnol.* 18:34-39 (2000).
Smith, "Brain Perfusion Systems for Studies of Drug Uptake and Metabolism in the Central Nervous System," *Pharm Biotechnol.* 285-307 (1996).
Smith et al., "The Challenges of Genome Sequence Annotation or 'The Devil is in the Details'," *Nat Biotechnol.* 15:1222-1223 (1997).
Steiniger et al., "Chemotherapy of Glioblastoma in Rats Using Doxorubicin-loaded Nanoparticles," *Int J Cancer.* 109:759-767 (2004).
Tamai et al., "Structure-Internalization Relationship for Absorptive-Mediated Endocytosis of Basic Peptides at the Blood-Brain Barrier," *J Pharmacol Exp Ther.* 280:410-415 (1997).

Temsamani et al., "Vector-Mediated Drug Delivery to the Brain," *Expert Opin Biol Ther.* 1:773-782 (2001).
Terasaki et al., "New Approaches to in vitro Models of Blood-Brain Barrier Drug Transport," *Drug Discov Today.* 8:944-954 (2003).
Triguero et al., "Capillary Depletion Method for Quantification of Blood-Brain Barrier Transport of Circulating Peptides and Plasma Proteins," *J Neurochem.* 54:1882-1888 (1990).
Turner et al., "RNA Targeting With Peptide Conjugates of Oligonucleotides, siRNA and PNA," *Blood Cells Mol Dis.* 38:1-7 (2007).
Veronese et al., "PEGylation, Successful Approach to Drug Delivery," *Drug Discov Today.* 10:1451-1458 (2005).
Wang et al., "DNA/dendrimer Complexes Mediate Gene Transfer into Murine Cardiac Transplants ex Vivo," *Mol Ther.* 2:602-608 (2000).
Wells, "Additivity of Mutational Effects in Proteins," *Biochemistry.* 29:8509-8517 (1990).
Witt et al., "Peptide Drug Modifications to Enhance Bioavailability and Blood-Brain Barrier Permeability," *Peptides.* 22:2329-2343 (2001).
Xu et al., "In Vitro and In Vivo Evaluation of Actively Targetable Nanoparticles for Paclitaxel Delivery," *Int J Pharm.* 288:361-368 (2005).
Yepes et al., "Tissue-Type Plasminogen Activator Induces Opening of the Blood-Brain Barrier Via the LDL Receptor-Related Protein," *J Clin Invest.* 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res.* 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther.* 3:5 (2005).
Zhang et al., "siRNA-containing Liposomes Modified with Polyarginine Effectively Silence the Targeted Gene," *J Control Release.* 112:229-239 (2006).
Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood-Cerebrospinal Fluid Barriers," *Proc Natl Acad Sci U S A.* 93:4229-4234 (1996).
U.S. Appl. No. 12/601,803, filed Nov. 24, 2009, Beliveau et al.
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem.* 8:327-337 (1997).
Banks, "Leptin Transport Across the Blood-Brain Barrier: Implications for the Cause and Treatment of Obesity," *Curr. Pharm. Des.* 7:125-133 (2001).
Banks, "The Blood-Brain Barrier as a Cause of Obesity," *Curr. Pharm. Des.* 14:1606-1614 (2008).
Bicamumpaka et al., "In Vitro Cytotoxicity of Paclitaxel-Transferrin Conjugate on H69 Cells," *Oncol. Rep.* 5:1381-1383 (1998).
Demeule et al., "Drug Transport to the Brain: Key Roles for the Efflux Pump P-Glycoprotein in the Blood-Brain Barrier," *Vascul. Pharmacol.* 38:339-348 (2002).
Dooley et al., "An All D-amino Acid Opioid Peptide with Central Analgesic Activity from a Combinatorial Library," *Science* 266:2019-2022 (1994).
Eigenbrot et al., "X-Ray Structure of Glial Cell-Derived Neurotrophic Factor at 1.9 Å Resolution and Implications for Receptor Binding," *Nat. Struct. Biol.* 4:435-438 (1997).
Gabius et al., "Targeting of Neoglycoprotein-Drug Conjugates to Cultured Human Embryonal Carcinoma Cells," *J. Cancer Res. Clin. Oncol.* 113:126-130 (1987).
Gottschalk et al., "Protein Self-Association in Solution: The Bovine Pancreatic Trypsin Inhibitor Decamer," *Biophys. J.* 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation.* 5:19 (2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).

(56) References Cited

OTHER PUBLICATIONS

Karyekar et al., "Zonula Occludens Toxin Increases the Permeability of Molecular Weight Markers and Chemotherapeutic Agents Across the Bovine Brain Microvessel Endothelial Cells," *J. Pharm. Sci.* 92:414-423 (2003).
Kirsch et al., "Anti-Angiogenic Treatment Strategies for Malignant Brain Tumors," *J. Neurooncol.* 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem.* 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev.* 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther.* 16:1805-1812 (2008) (pp. 1-18).
Uekita et al., "Cytoplasmic Tail-Dependent Internalization of Membrane-Type 1 Matrix Metalloproteinase is Important for its Invasion-Promoting Activity," *J. Cell. Biol.* 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem.* 279:12734-12743 (2004).
Akhtar et al., "Nonviral Delivery of Synthetic siRNAs in Vivo," *J. Clin. Invest.* 117: 3623-3632 (2007).
Anonymous, "Blood-Brain Barrier Tackled," <http:www.ecancermedicalscience.com/news-insider-news.asp?itemld=326> Oct. 22, 2008.
Bertrand et al., "Transport Characteristics of a Novel Peptide Platform for CNS Therapeutics," *J. Cell Mol. Med.* published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res.* 41:98-107 (2008).
Ché et al., "New Angiopep-Modified Doxorubicin (ANG1007) and Etoposide (ANG1009) Chemotherapeutics with Increased Brain Penetration," *J. Med. Chem.* 53: 2814-2824 (2010).
Demeule et al., "Involvement of the Low-Density Lipoprotein Receptor-Related Protein in the Transcytosis of the Brain Delivery Vector Angiopep-2," *J. Neurochem.* 106: 1534-1544 (2008).
Garsky et al., "The Synthesis of a Prodrug of Doxorubicin Designed to Provide Reduced Systemic Toxicity and Greater Target Efficacy," *J. Med. Chem.* 44: 4216-4224 (2001).
Huang et al., "Targeting Delivery of Paclitaxel into Tumor Cells via Somatostatin Receptor Endocytosis," *Chem. Biol.* 7: 453-461 (2000).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol.* 57: 679-686 (2000).
Takei et al., "A Small Interfering RNA Targeting Vascular Endothelial Growth Factor as Cancer Therapeutics," *Cancer Res.* 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 13, 2011, Demeule et al.
Grimm et al., "Ten Year Biochemical Outcomes Following 125-Iodine Monotherapy for Early Stage Prostate Cancer." *Int. H. Rad.* 48:146-147 (2000).
Kurzrock et al., "ANGI005: Results of a Phase I study in patients with advanced solid tumors and metastatic brain cancer" Poster B168, ACCR/NCL/EORTC Annual Meeting, 2009.
Mathupala, "Delivery of Small-interfering RNA (siRNA) to the Brain," *Exp. Opin. Ther. Pat.* 19: 137-140, (2009).

Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans.* 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet.* 118:31-37 (2010).
International Search Report and Written Opinion of the International Searching Authority for Application No. PCT/CA2009/000542, mailed on Jul. 21, 2009.
U.S. Appl. No. 61/138,375, Beliveau et al.
Author manuscript of Hein et al., "Click chemistry, a powerful tool for pharmaceutical sciences," published in final edited form as: Pharm Res. 25(10):2216-2230 (2008).
Author manuscript of Howes et al., "Rapid induction of therapeutic hypothermia using convective-immersion surface cooling: Safety, efficacy and outcomes," published in final edited form as: Resuscitation. 81:388-392 (2010).
Belkin et al., "Matrix-dependent proteolysis of surface transglutaminase by membrane-type metalloproteinase regulates cancer cell adhesion and locomotion," J Biol Chem. 276(21):18415-18422 (2001).
Boado et al., "GDNF fusion protein for targeted-drug delivery across the human blood-brain barrier," Biotechnol Bioeng. 100(2):387-96 (2008).
Brady et al., "Drug design. Refelections on a peptide." Nature. 368(6473):692-693 (1994).
Buvanendran et al., "Recent advances in nonopioid analgesics for acute pain management," Tech Reg Anesth Pain Man. 11(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmocol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).
Demuie et ai., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010).
DeWitt et al., "'Diversomers': an approach to nonpeptide, nonoligomeric chemical diverstiy," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).

(56) References Cited

OTHER PUBLICATIONS

Evans et al., "Design of nonpeptidal ligands for a peptide receptor: Cholecystokinin antagonists," J Med Chem. 30(7):1229-1239 (1987).
Fauchere et al., "Association with HeLa cells of *Campylobacter jejuni* and *Campylobacter coli* isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approcaches to the transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4S)-hydroxymethyl-(2R)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpressions of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Howes et al., "Rapid induction of therapeutic hypothermia using convective-immersion surface cooling: safety, efficacy and outcomes," Resuscitation. 81(4):388-392 (2010).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
J.E. Lachowicz et al., "Analgesic properties of a novel brain-penetrant Angiopep-2-neurotensin derivative (ANG2002) for treating chronic pain," *Program No. 173.28/AA9 2012 Neuroscience Meeting Planner*, New Orleans, LA: Society for Neuroscience (2012).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).

Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochem Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Impaired tyrosine phosphorylation of membrane type 1-matrix metalloproteinase reduces tumor cell proliferation in three-dimensional matrices and abrogates tumor growth in mice," Carcinogenesis. 29(8):1655-64 (2008).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).

(56) References Cited

OTHER PUBLICATIONS

Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 47(1):118-26 (2010).
Spatola et al., "Structure-activity relationships of enkephalins containing serially replaced thiomethylene amide bond surrogates," Life Sci. 38(14):1243-9 (1986).
UniProtKB Entry P08183 (MDR1_HUMAN), "Multidrug resistance proteins 1(EC 3.63.44) (ATP-binding cassette DE subfamily B member 1) (P-glycoprotein 1) (CD243 antigen)," Sep. 18, 2013 (16 pages).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):65436550 (2005).
Zhang et al. "In vitro gene delivery using polyamidoamine dendrimers with a trimesyl core," Biomacromolecules. 6(1):341-350 (2005).
Decision of Rejection with English Translation for Japanese Patent Application No. 2008-520685, mailed on Feb. 14, 2013 (8 pages).
Examination Report for Australian Application No. 2009238187, dated Feb. 7, 2013 (4 pages).
Extended European Search Report for European Patent Application No. 09733078.1, dated Aug. 7, 2013 (6 pages).

\* cited by examiner

PHARMACEUTICAL COMPOSITIONS OF PACLITAXEL, PACLITAXEL ANALOGS OR PACLITAXEL CONJUGATES AND RELATED METHODS OF PREPARATION AND USE

CROSS-REFERENCE TO RELATED APPLICATIONS

This application is the national stage of International Application No. PCT/CA2009/000542, filed Apr. 20, 2009, which claims the benefit of U.S. Provisional Application No. 61/124,677, filed Apr. 18, 2008.

INCORPORATION BY REFERENCE OF A SEQUENCE LISTING FILED ELECTRONICALLY

Kindly incorporate the .txt file Sequence Listing concurrently filed with this application electronically having the name 50546_007002_ST25.txt, file size 32.3 kB, created on Oct. 14, 2010.

BACKGROUND OF THE INVENTION

The invention relates to formulations of paclitaxel and paclitaxel analogs, or conjugates thereof, as well as other hydrophobic agents.

Due to insolubility in aqueous solution, hydrophobic agents, such as paclitaxel and paclitaxel analogs, typically are either solubilized in non-aqueous or surfactant buffers or attached to hydrophilic moieties for increased solubility in aqueous solution prior to administration to a patient. Paclitaxel is commercially supplied in a formulation where each ml contains 6 mg paclitaxel, 527 mg of purified CREMOPHOR® EL (polyoxyethylated castor oil) and 49.7% (v/v) dehydrated alcohol, USP and ethanol. Prior to administration, the formulated paclitaxel is diluted in a sodium chloride/dextrose or dextrose in Ringer's solution. Because CREMOPHOR® can cause hypersensitivity (e.g., anaphylactic) reactions, patients receiving paclitaxel are premedicated with dexamethasone to reduce the occurrence of these reactions. Because of these reactions, paclitaxel is administered over 4 hours to minimize the hypersensitivity effects.

Because of the high rate of side effects due to the inclusion of CREMOPHOR® in the standard paclitaxel formulations, alternate formulations have been created. These formulations rely upon association of paclitaxel with a soluble compound. Abraxane is paclitaxel formulation where paclitaxel is bound to albumin. Liposomal paclitaxel formulations have also been proposed.

Because the existing formulations of hydrophobic agents, such as paclitaxel, either contain undesirable excipients or can be difficult to manufacture, there is a need for new formulations of such agents.

In first aspect, the invention features a composition including (a) a hydrophobic agent, paclitaxel, a paclitaxel analog, or a conjugate (e.g., ANG1005) including (i) a polypeptide vector; and (ii) a therapeutic agent selected from the group consisting of paclitaxel and a paclitaxel analog, where the therapeutic agent is conjugated to a polypeptide, or any hydrophobic agent described herein); (b) an optional tonicity agent (e.g., sodium chloride or any tonicity agent described herein); (c) a buffering agent (e.g., glycine, lactic acid, or citric acid, or any buffering agent described herein); (d) a bulking agent (e.g., mannitol, sorbitol, or any bulking agent described herein); and (e) a solubilizing agent (e.g., polyoxyethylene ester of a fatty acid such as SOLUTOL®HS 15, or any solubilizing agent described herein), for example, where the solubilizing agent is not CREMOPHOR®. The polypeptide vector may include an amino acid sequence substantially identical (e.g., at least 70%, 80%, 90%, 95%, or 100% identical) to an amino acid sequence selected from the group consisting of SEQ ID NOS:1-105 and 107-116 (e.g., Angio-Pep-1 (SEQ ID NO:67); AngioPep-2 (SEQ ID NO:97), or AngioPep-7 (SEQ ID NO:112)). In certain embodiments, the buffering agent maintains the solution at a pH of less than 6 (e.g., pH 4-6). In certain embodiments, the composition further includes 0.01-10% (e.g., less than 8%, 6%, 5%, 4%, 3%, 2%, 1%, 0.75%, 0.5%, 0.2%, or 0.1%) DMSO. In certain embodiments, the composition is substantially free from CREMOPHOR® (e.g., free of CREMOPHOR®). The composition may be dissolved in water.

In certain embodiments, the composition comprises agents in the amounts shown in any of Tables 1-4.

TABLE 1

| Compound | Percentage (by non-water weight) |
|---|---|
| ANG1005 | 0.1-5% |
| Tonicity agent | 0-15% |
| Buffering agent | 1-10% |
| Bulking agent | 0-15% |
| SOLUTOL ® HS 15 | 40-75% |
| DMSO | 0.01-10% |

TABLE 2

| Compound | Percentage (by non-water weight) |
|---|---|
| ANG1005 | 1.8-2.3% |
| Tonicity agent | 9-11% |
| Buffer | 4.5-6% |
| Bulking agent | 8-10% |
| SOLUTOL ® HS 15 | 69-75% |
| DMSO | 0.2-1% |

TABLE 3

| Compound | Percentage (by non-water weight) |
|---|---|
| ANG1005 | 1.8-4.0% |
| Buffer | 0.1-6% |
| Bulking agent | 2-10% |
| SOLUTOL ® HS 15 | 80-95% |
| DMSO | 0.2-1% |

TABLE 4

| Compound | Percentage (by non-water weight) |
|---|---|
| ANG1005 | 2.0-3.0% |
| Buffer | 0.5-6% |
| Bulking agent | 4-7% |
| SOLUTOL ® HS 15 | 85-95% |
| DMSO | 0.2-0.6% |

In these compositions, the tonicity agent, if present, may be sodium chloride, the buffering agent may be glycine, lactic acid, or citric acid, and/or the bulking agent may be mannitol. The composition may be made up of about 0.1%, 0.2%, 0.3%, 0.4%, 0.5%, 0.6%, 0.7%, 0.8%, 0.9%, 1.0% 1.1, 1.2, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 3.0%, 3.2%, 3.5%, 4.0%, or 5.0% ANG1005, or any range in between any of these values. The ANG1005 may be dissolved in a sufficient amount of SOLUTOL® HS 15, and/or DMSO, which may be further diluted in an aqueous solution.

The above compositions may be present in a container that may be sealed. The container may be part of a kit that further includes instructions for use (e.g., for administering the composition for treatment of any disease such as those described herein).

In another aspect, the invention features a method of administering a composition of the above aspects to patient suffering from a disease, for example, any disease described herein such as cancer (e.g., ovary, brain, lung, liver, spleen, or kidney cancer The method includes administering to the patient the composition in an amount sufficient to treat or treat prophylactically the disease. In certain embodiments, the cancer is a brain cancer selected from the group consisting of glioblastoma, astrocytoma, glioma, meduloblastoma, and oligodendroma, neuroglioma, ependymoma, and meningioma.

In another aspect, the invention features a method for preparing a pharmaceutical composition. The method includes (a) dissolving a hydrophobic agent in a first solubilizing agent (e.g., DMSO or any such agent described herein) to form a mixture; (b) adding a second solubilizing agent (e.g., a polyoxyethylene ester of a fatty acid such as SOLUTOL® HS 15, or any such agent described herein) to the mixture of step (a); (c) optionally adding water and a buffering agent to the mixture; (d) lyophilizing mixture of step (c); where the lyophilization results in a reduction of at least 5% (e.g., 10%, 20%, 30%, 50%, 75%, 90%, 95%, or 99%) of the amount of the first solubilizing agent (e.g., to a final proportion of less than 0.2%, 0.4%, 0.6%, 0.8%, 1.0%, 1.5%, 2%, 3%, 4%, 5%, 8% of the total weight of the lyophilized product). In certain embodiments, the lyophilizing does not substantially reduce the amount of the second solubilizing agent. In certain embodiments, the hydrophobic agent includes paclitaxel or a paclitaxel analog. The hydrophobic agent may include or may be a conjugate including (a) a polypeptide vector and (b) an agent described herein (e.g., paclitaxel and analogs thereof), where the agent is conjugated to the vector. The polypeptide vector may be substantially identical to an amino acid sequence selected from the group consisting of SEQ ID NOS: 1-105 and 107-116 (e.g., AngioPep-1 (SEQ ID NO:67); AngioPep-2 (SEQ ID NO:97), or AngioPep-7 (SEQ ID NO:112)). In particular embodiments, the conjugate is ANG1005. In certain embodiments, water and a buffering agent are added in step (c) and the step (d) lyophilizing includes (i) freezing the mixture; (ii) drying the frozen product at a first temperature and pressure sufficient to remove at least a portion (e.g., at least 50%, 60%, 70%, 80%, 90%, 95%, 99%, 99.5%, 99.9%, or 99.99%) of the water; and (iii) drying the product at a second temperature and pressure sufficient to remove at least a portion (e.g., at least 5% (e.g., 10%, 20%, 30%, 50%, 75%, 90%, 95%, or 99%) of the first solvent. The mixture of step (b) may be filtered prior to step (c) lyophilizing or may be placed into a vial or container prior to step (c) lyophilizing. The method may further include (c) resuspending the lyophilized product.

In another aspect, the invention features a method for producing a pharmaceutical composition including the steps (a) dissolving in DMSO a conjugate including paclitaxel or paclitaxel analog conjugated to a polypeptide vector, thereby forming a mixture; (b) adding SOLUTOL® HS 15 to the mixture; (c) adding water, a buffering agent, and optionally salt or a bulking agent to the mixture; and (d) lyophilizing the mixture under conditions which remove the water and the DMSO from the mixture. The SOLUTOL® HS 15 may be mixed with water, a buffering agent, and optionally a tonicity agent or a bulking agent prior to adding to the mixture, where the water, buffering agent, and optional tonicity agent are added in a amount which maintains solubility of the conjugate in the mixture. The buffering agent may maintain the solution at a pH between 4 and 6. The DMSO may be acidified between pH 3.5 and 4.5 prior to the step (a) dissolving. In certain embodiments, the lyophilization does not substantially reduce the amount of SOLUTOL® HS 15 in the mixture. The conjugate may include any of the polypeptides (e.g., AngioPep-2) described herein. In particular embodiments, the paclitaxel-polypeptide conjugate is ANG1005.

In another aspect, the invention features a pharmaceutical composition produced by any of the methods described above.

By "buffering agent" is meant any compound or group of compounds capable of maintaining the pH (e.g., between any of pH 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, and 13.5) of a solution within a particular range upon addition of agents that can otherwise alter the pH. Exemplary buffering agents are described herein.

By "tonicity agent" is meant any agent that alters the osmolarity of an aqueous solution (e.g., any of or any range between 10, 20, 50, 75, 100, 150, 200, 250, 300, 400, 500, 750, 1000, 1500, or 2000 mM). Ionic salts, such as sodium chloride, can be used to adjust tonicity. Additional tonicity agents are described herein.

By "bulking agent" is meant a compound that alters the physical form of a chemical composition following a dehydration or lyophilization procedure. Exemplary bulking agents are described herein.

By "solubilizing agent" is meant any solvent capable of dissolving a particular compound (e.g., a hydrophobic compound such a compound or conjugate containing paclitaxel or a paclitaxel analog). Exemplary solubilizing agents suitable for hydrophobic compounds are described herein.

By "vector" is meant a compound or molecule such as a polypeptide that can be transported into a particular cell type (e.g., liver, lungs, kidney, spleen, or muscle) or across the BBB. The vector may be attached to (covalently or not) or conjugated to an agent and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "conjugate" is meant a vector linked to an agent. The conjugation may be chemical in nature, such as via a linker, or genetic in nature for example by recombinant genetic technology, such as in a fusion protein with for example a reporter molecule (e.g., green fluorescent protein, β-galactosidase, Histag, etc.).

By a vector or conjugate which is "efficiently transported to a particular cell type" is meant a vector or conjugate that is able to accumulate (e.g., either due to increased transport into the cell, decreased efflux from the cell, or a combination thereof) in that cell type at least 10% (e.g., 25%, 50%, 100%, 200%, 500%, 1,000%, 5,000%, or 10,000%) greater extent than either a control substance, or, in the case of a conjugate, as compared to the unconjugated agent.

By "substantially pure" or "isolated" is meant a compound (e.g., a polypeptide or conjugate) that has been separated from other chemical components. Typically, the compound is substantially pure when it is at least 30%, by weight, free from other components. In certain embodiments, the preparation is at least 50%, 60%, 75%, 85%, 90%, 95%, 96%, 97%, 98%, or 99% by weight, free from other components. A purified polypeptide may be obtained, for example, by expression of a recombinant polynucleotide encoding such a polypeptide or by chemically synthesizing the polypeptide. Purity can be measured by any appropriate method, for example, column chromatography, polyacrylamide gel electrophoresis, or by HPLC analysis.

A pharmaceutical composition which is "substantially free" from a substance means that the amount of a substance in the composition is less than 5%, 4%, 3%, 2%, 1%, 0.5%, 0.3%, 0.2%, 0.1%, 0.05%, or 0.01% of the dry weight of a composition.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs which are identical or similar to amino acids of the original polypeptide. The gaps may include no amino acids, one or more amino acids which are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "fragment" is meant a polypeptide originating from a portion of an original or parent sequence or from an analogue of said parent sequence. Fragments encompass polypeptides having truncations of one or more amino acids, wherein the truncation may originate from the amino terminus (N-terminus), carboxy terminus (C-terminus), or from the interior of the protein. A fragment may include the same sequence as the corresponding portion of the original sequence. Functional fragments of the vector (polypeptide) described herein are encompassed by the invention. Fragments may be at least 5 (e.g., at least 5, 6, 7, 8, 9, 10, 11, 12, 13, 14, 15, 16, 17, 18, 19, 20, 21, 22, 23, 25, 28, 30, 35, 40, 45, 50, 60, 75, 100, or 150) amino acids. Fragments of the invention may include, for example, a polypeptide of 7, 8, 9 or 10 amino acids to 18 amino acids. Fragments may contain any of the modifications described herein (e.g., acetylation, amidation, amino acid substitutions)

A "non-naturally occurring amino acid" is an amino acid that is not naturally produced or found in a mammal.

By "agent" is meant any compound, for example, an antibody, or a therapeutic agent, a marker, a tracer, or an imaging compound.

By "therapeutic agent" is meant an agent having a biological activity. In some cases, the therapeutic agent is used to treat the symptoms of a disease, a physical or mental condition, an injury, or an infection and includes anti-cancer agents, antibiotics, anti-angiogenic agents, and molecules active at the level of the central nervous system.

By "small molecule drug" is meant a drug having a molecular weight of 1000 g/mol or less (e.g., less than 800, 600, 500, 400, or 200 g/mol).

By "subject" is meant a human or non-human animal (e.g., a mammal).

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence of (e.g., preventing) a disease, disorder or condition by administering a therapeutic agent to the subject.

By "cancer" is meant any cellular proliferation whose unique trait is the loss of normal controls which can result in unregulated growth, lack of differentiation, or ability to invade tissues and metastasize. Cancer can develop in any tissue or in any organ. Cancer is intended to include, without limitation, cancer of the brain, liver, lungs, kidney, or spleen. Additional cancers are described herein.

By "administering" and "administration" is meant a mode of delivery including, without limitation, orally, intra-arterially, intra-nasally, intraperitoneally, intravenously, intramuscularly, subcutaneously, transdermally or per os. A daily dosage can be divided into one, two or more doses in a suitable form to be administered at one, two or more times throughout a time period.

By "therapeutically effective" or "effective amount" is meant an amount of a therapeutic agent sufficient to improve, decrease, prevent, delay, suppress, or arrest any symptom of the disease or condition being treated. A therapeutically effective amount of an agent need not cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

If a "range" or "group of substances" is mentioned with respect to a particular characteristic (e.g., temperature, concentration, time and the like), the invention relates to and explicitly incorporates herein each and every specific member and combination of sub-ranges or sub-groups therein. Thus, for example, with respect to a length of from 9 to 18 amino acids, is to be understood as specifically incorporating herein each and every individual length, e.g., a length of 18, 17, 15, 10, 9, and any number therebetween. Therefore, unless specifically mentioned, every range mentioned herein is to be understood as being inclusive. For example, in the expression from 5 to 19 amino acids long is to be as including 5 and 19. This similarly applies with respect to other parameters such as sequences, length, concentrations, elements, and the like.

The sequences, regions, portions defined herein each include each and every individual sequence, region, and portion described thereby as well as each and every possible sub-sequence, sub-region, and sub-portion whether such sub-sequences, sub-regions, and sub-portions are defined as positively including particular possibilities, as excluding particular possibilities or a combination thereof. For example, an exclusionary definition for a region may read as follows: "provided that said polypeptide is no than 4, 5, 6, 7, 8 or 9 amino acids. A further example of a negative limitation is the following; a sequence including SEQ ID NO:X with the exclusion of a polypeptide of SEQ ID NO:Y; etc. An additional example of a negative limitation is the following; provided that said polypeptide is not (does not include or consist of) SEQ ID NO:Z.

Other features and advantages of the invention will be apparent from the following Detailed Description, the drawings, and the claims.

DETAILED DESCRIPTION

Figure 1:
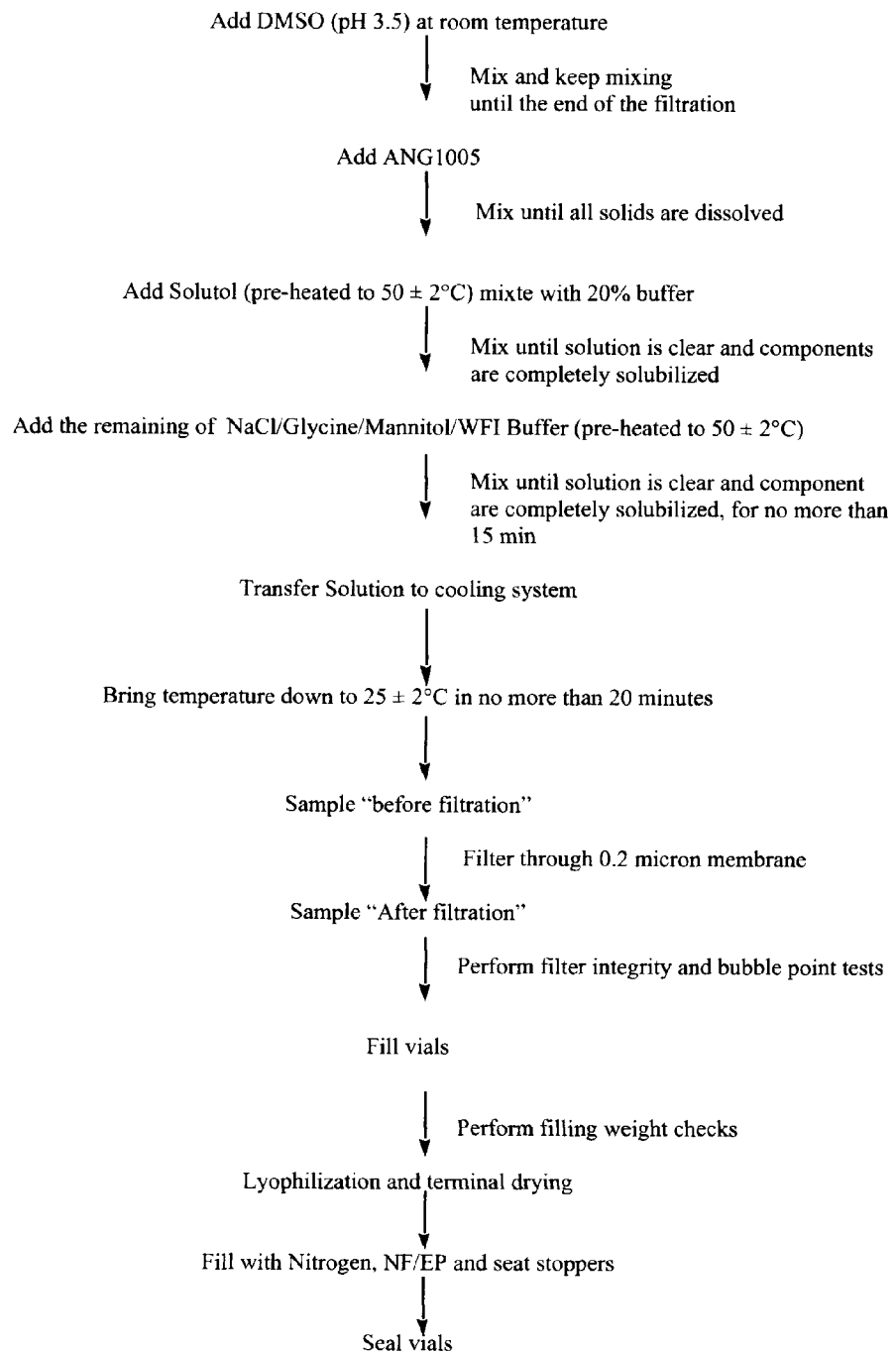
FIG. 1 is a schematic depiction of an exemplary method for preparing a pharmaceutical composition including ANG1005.

We have developed pharmaceutical formulations useful; for hydrophobic therapeutic agents, including paclitaxel and paclitaxel analogs, or conjugates thereof (e.g., ANG1005) and methods for making and administering pharmaceutical compositions with such formulations. Hydrophobic therapeutic agents (e.g., paclitaxel) are often solubilized indeed, often require) hydrophobic solvents. Commonly used solvents for paclitaxel include CREMOPHOR® and DMSO, which may not be well tolerated by patients. CREMOPHOR®, in particular, can cause anaphylactic reactions, thus requiring pretreatment with agents such as corticosteroids. To avoid using such poorly tolerated solvents, we have developed new formulations for the exemplary polypeptide-paclitaxel conjugate, ANG1005. The formulations described herein are advantageous in that they can manufactured without the use of CREMOPHOR®, can be prepared to contain minimal DMSO concentrations, result in low degradation and high activity of the active agent, and can be manufactured using conventional methods. Compositions that do not contain poorly tolerated excipients can be administered to patients in higher doses, can be administered more rapidly (e.g., in the case of intravenous administration), can be administered more frequently, or may avoid the need to for pretreatments with agents (e.g., corticosteroids) to increase tolerance to such excipients.

Development of a Formulation for ANG1005

In developing a new formulation of the exemplary hydrophobic agent, ANG1005, we first tested its solubility in various solvents and combinations of solvents. As outlined in Example 1, and as with paclitaxel, ANG1005 has low solubility in aqueous solutions but is highly soluble in DMSO (120 mg/ml). ANG1005 was also soluble in SOLUTOL® HS 15 (BASF, Parsippany, N.J.) with ethanol at 75° C. (6 mg/ml). Because of its low toxicity and compatibility with the drug, SOLUTOL® HS 15 was selected as a solubilization agent. However, dissolving in SOLUTOL® HS 15 by itself resulted in significant degradation of the ANG1005. To dissolve ANG1005, SOLUTOL® HS 15 was heated to at least 65° C. In addition, we noted that heating unbuffered SOLUTOL® from 25° C. to 50° C. increased its pH from 6.0 to 9.0. Thus, the combination of high temperature and high pH likely contributes to the observed instability of ANG1005 under these conditions.

To avoid excessive degradation, ANG1005 was first dissolved in acidified DMSO (pH 3.5-4.0) prior to addition of 50° C. SOLUTOL® (see Example 2). To further stabilize the ANG1005, we acidified the SOLUTOL® HS 15 by premixing with glycine buffer at pH 5.0, which maintains solubility of the ANG1005. Doing so minimizes the degradation of the ANG1005. It is possible to add up to 20% (e.g., 1%, 5%, 10%, or 15%) of the buffer to the SOLUTOL® prior to the addition of ANG1005 without effecting solubility of ANG1005, whereas mixing a larger amount of buffer with the SOLUTOL® results in incomplete solubilization.

To ensure ANG1005 stability, the formulation was diluted in aqueous solution buffered at pH 5 with glycine, as we have observed that ANG1005 becomes increasingly unstable at pH 6 and above. Other buffers in this pH range were evaluated, including acetate, and phosphate, but these were less compatible with the formulation. We also attempted to stabilize the ANG1005 by reducing the final pH to 4, but the resulting lyophilized cake did not reconstitute to a clear solution.

An exemplary ANG1005 composition is provided in Table 5 below.

TABLE 5

Component Function in ANG1005 for Injection

| Component | Purpose | Target Amount/ Batch | Target Amount/vial |
|---|---|---|---|
| ANG1005 | API | 60 g | 120 mg |
| Sodium chloride, USP | Osmolarity | 290 g | 580 mg |
| Glycine | Buffer | 150 g | 300 mg |
| Mannitol | Bulking agent | 260 g | 520 mg |
| SOLUTOL ® HS 15 | Solubilization of API | 2000 ml | 4 ml |
| DMSO | Solubilization of API pre-lyophilization | 500 ml$^1$ | 1 ml$^1$ |
| HCl | pH adjustment | to adjust pH | |
| Water for Injection, USP | Solvent | QS to 10 L$^1$ | to 20 ml$^1$ |

$^1$Removed by Lyophilization

Bulking agents were also added to facilitate the reconstitution of the lyophilized product. Both mannitol and sorbitol containing formulations were evaluated. Mannitol yielded a superior cake.

Lyophilization

Because the DMSO/SOLUTOL®/buffer preparation contained undesirably high levels of DMSO and was not sufficiently stable, a lyophilization protocol designed to reduce the DMSO and to increase ANG1005 stability was developed. A number of alternative lyophilization cycles were evaluated to minimize DMSO content (i.e., increasing temperature and length of secondary drying; see Example 3). Lyophilization conditions are described in detail below. A first lyophilization protocol was attempted, and this procedure resulted in DMSO concentrations greater than 1%. Details of this procedure are shown in Table 6.

TABLE 6

Lyophilization Cycle for ANG1005 for Injection

| Step | Temperature | Vacuum | Hold Time |
|---|---|---|---|
| Loading | ≤−40° C. | Atmospheric | N/A |
| Freezing | ≤−40° C. | Atmospheric | 3 ± 1 hour |
| Primary Drying | ≥−25° C. | 50 mT | 90 ± 1 hours |
| Secondary Drying | ≥22° C. | 50 mT | 9 ± 1 hour |
| Stoppering | ≥22° C. | 5-10 mmHg | N/A |

We have been able to reduce the DMSO concentration further, to less than 1%, by using an optimized two-step drying procedure. Briefly, following freezing of the product, lyophilization is carried out at a shelf temperature and for a time sufficient to remove most of the water from the product. The shelf temperature is raised, and the product is dried a temperature suitable for DMSO removal. The precise conditions will vary depending on the volume of the sample being dried, the pressure and the temperatures used and the formulation and buffers used Based on the procedure described herein, one of skill in the art would be able to determine appropriate drying conditions to generate the compositions described herein.

In one exemplary procedure, the formula is loaded at a temperature between −70 and +25° C. (e.g., −40° C.). The temperature is then ramped to a set temperature sufficient to freeze the solution (any temperature between 0° C. and −70° C. such as −40° C.) and the temperature is held at that temperature for a time sufficient to freeze the product, and preferably for a time sufficient to ensure that the lyophilization cake does not collapse. We determined that, at −40° C., at least 12 hours (e.g., at least 15, 18, 20, 24, 36, or 48 hours) of freezing time was required to ensure the cake did not collapse. Following freezing, the vacuum was set to a pressure (e.g., 10-500 mT such as 20, 50, 100, 200, or 500 mT) and temperature (e.g., −15 to −35° C. such as −25° C.) sufficient to remove the water from the product for the primary drying cycle. To this end, pressures between 10-100 mT were tested with minimal variation in results. The drying time can be for a time sufficient (e.g., at least 6 hours, 12 hours, 1 day, 2 days, 4 days, 6 days, 8 days, 10 clays, or 14 days) to remove a substantial portion (e.g., at least 50%, 60%, 70%, 80%, 90%, 95%, 98%, 99%, 99.5%, 99.9%) of the water present in the product. Following the primary drying cycle, a secondary drying cycle to remove DMSO was performed. The product was ramped to a higher temperature between 10-30° C. (e.g., 18, 19, 20, 21, 22, 23, 24, 25, 26, or 27° C.) to remove the DMSO. In a preferred embodiment, the shelf temperature is ramped to 27° C. over 2 hours, and then held at 27° C. for one hour. The shelf temperature is then ramped (or maintained) between 23 and 27° C. over 30 minutes and then held at that temperature for at least another 10 hours (e.g., at least 15, 20, 25, 30, 40, 48, 60, or 72 hours). To prevent the residual DMSO from melting, the product can be kept below 25° C. An exemplary protocol for this method is shown in Table 7. Lyophilization was performed using a Hull Freezer Dryer, Model 72FS100-SS20C.

TABLE 7

| Segment | Operation | Temperature | Time |
|---|---|---|---|
| 1 | Load Set Point | −40° C. | N/A |
| | FREEZE DOWN | | |
| 2 | Ramp Shelf to | −40° C. | 0 minutes |
| 3 | Hold Shelf at | −40° C. | 420-1440 minutes |
| | PRIMARY DRYING | | |
| | Set vacuum control to 50 mT & condenser control set to −50° C. for step 4-7 | | |
| 4 | Ramp Shelf to | −25° C. | 120 minutes |
| 5 | Hold Shelf at | −25° C. | 5760 minutes |
| | SECONDARY DRYING | | |
| 6 | Ramp Shelf to | 27° C. | 120 minutes |
| 7 | Hold Shelf at | 27° C. | 60 minutes |
| 8 | Ramp Shelf to | 23-27° C. | 30 minutes |
| 9 | Hold Shelf at | 23-27° C. | 900-1200 minutes |

Reconstitution of the Product

Prior to injection into a patient or laboratory analysis of the product, the lyophilized product can be reconstituted. Any buffer, solvents, or combination of buffer(s) and solvent(s) suitable for reconstitution can be used; the precise buffer is not critical. It is, however, often desirable that the active agent is sufficiently stable in the solution and that the buffer(s) or solvent(s) used be sufficiently well tolerated by patients in solutions for administration to patients. In case of ANG1005, because the product is less stable at pH above 6.0, it is generally desirable to use a reconstitution solvent/buffer system which maintains a pH below 6.0. For ANG1005, one preferred solvent system is a combination of ethanol and lactated Ringers/5% Dextrose. In this system, ethanol is added to the vial containing the product, gently mixed, and then the lactated Ringers/5% Dextrose is added to dissolve the product. The use of conventional water for injection (WFI) or saline as diluents yielded high pH levels, leading to degradation of ANG1005. Following dissolution, the mixture may be further diluted in water or other buffer systems. Exemplary conditions for reconstitution of the lyophilized product are described further in Example 4 below.

Formulation Compositions

As described above, we have developed formulations of the exemplary hydrophobic agent, ANG1005 suitable for administration to patients. Prior to lyophilization, the formulation may, in certain embodiments, contain a significant proportion of DMSO. Such compositions may have the following components (e.g., dry weight) as show in Tables 8A and 8B. Table 8C shows exemplary concentrations of the various component in aqueous solution prior to lyophilization.

TABLE 8A

Percentage by weight not including water

| Compound | Percentage (by weight) | Preferred percentages | Exemplary Percentages |
|---|---|---|---|
| ANG1005 | 0.1-5% | 1-3% | 1.8% |
| Tonicity agent (e.g., sodium chloride) | 1-15% | 5-12% | 8.6% |
| Buffer (e.g., glycine) | 1-10% | 3-7% | 4.5% |
| Bulking agent (e.g., mannitol) | 0-15% | 5-12% | 7.7% |
| SOLUTOL ® HS 15 | 40-75% | 50-70% | 61.1% |
| DMSO | 3-20% | 10-20% | 16.3% |

TABLE 8B

Percentage in aqueous solution (prelyophilization)

| Compound | Percentage (by weight) | Preferred percentages | More Preferred Percentages | Exemplary Percentages |
|---|---|---|---|---|
| ANG1005 | 0.05-1.5% | 0.1-1.0% | 0.2-0.8% | 0.55% |
| Tonicity agent (e.g., sodium chloride) | 0.1-10% | 0.5-6% | 1-3% | 2.7% |
| Buffer (e.g., glycine) | 0.05-5%- | 0.1-4% | 0.5-1.5% | 1.4% |
| Bulking agent (e.g., mannitol) | 0-5% | 0.2-4% | 1.0-3.0% | 2.4% |
| SOLUTOL ® HS 15 | 1-40% | 3-30% | 10-25% | 19.0% |
| DMSO | 0.5-15% | 1-10% | 2-8% | 5.0% |
| Water | 25-85% | 50-80% | 65-75% | 69.0% |

TABLE 8C

| | Concentrations (mg/ml) prelyophilization aqueous solution | | | |
|---|---|---|---|---|
| Compound | Concentration (mg/ml) | Preferred Concentrations | More Preferred Concentrations | Exemplary Concentrations |
| ANG1005 | 0.1-10.0 | 2-7 | 4-6.5 | 6.0 |
| Tonicity agent (e.g., sodium chloride) | 5-200 | 10-100 | 10-50 | 29 |
| Buffer (e.g., glycine) | 1-200 | 3-100 | 5-25 | 15 |
| Bulking agent (e.g., mannitol) | 0-100 | 2-50 | 5-35 | 26 |
| SOLUTOL ® HS 15 | 10-400 | 20-300 | 50-250 | 206 |
| DMSO | 1-200 | 15-200 | 30-100 | 55 |

The composition is typically diluted into in water prior to lyophilization (see below regarding lyophilization conditions). For most clinical applications, the solution is divided into appropriate amounts for single dose administration of ANG1005 (e.g., about 10, 20, 30, 60, 90, 120, 150, 200, 240, 300, 400, or 500 mg). Following lyophilization (e.g., under the conditions described herein), DMSO concentration can be reduced significantly. Following lyophilization, an ANG1005 composition of the invention may have the following characteristics (e.g., dry weight) as shown in Table 9.

TABLE 9

| Compound | Percentage (by weight) | Preferred percentages | More preferred percentages | Exemplary percentages (0.5% DMSO) |
|---|---|---|---|---|
| ANG1005 | 0.1-5% | 1.5-3% | 1.8-2.3% | 2.11 |
| Tonicity agent (e.g., sodium chloride) | 0-15% | 0-12% | 9-11% | 10.18 |
| Buffer (e.g., glycine) | 1-10% | 3-7% | 4.5-6% | 5.27 |
| Bulking agent (e.g., mannitol) | 0-15% | 5-12% | 8-10% | 9.13 |
| SOLUTOL ® HS 15 | 40-75% | 50-70% | 69-75% | 72.32 |
| DMSO | 0.01-10% | 0.1-5% | 0.2-0.5 | 0.50 |

Hydrophobic Agents

Any hydrophobic agents may be used in the compositions and methods of the present invention. Exemplary compounds are described below.

Paclitaxel and Related Compounds

While the invention has been exemplified using ANG1005, an AngioPep2-paclitaxel conjugate, the formulations described herein may be used with paclitaxel, paclitaxel analogs, or conjugates thereof. Paclitaxel has the formula:

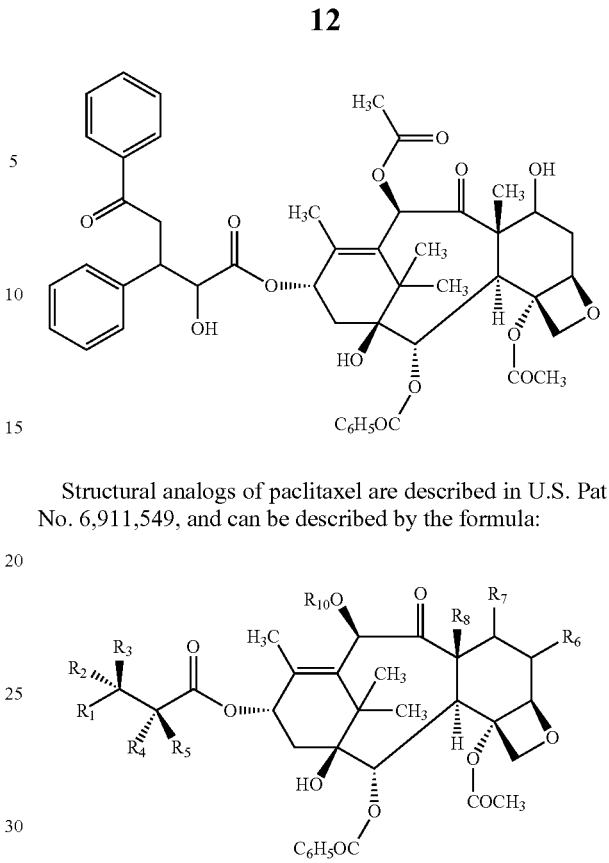

Structural analogs of paclitaxel are described in U.S. Pat. No. 6,911,549, and can be described by the formula:

wherein $R_1$ is selected from the group consisting of —$CH_3$; —$C_6H_5$, or phenyl substituted with one, 2 or 3 $C_1$-$C_4$ alkyl, $C_1$-$C_3$ alkoxy, halo, $C_1$-$C_3$ alkylthio, trifluoromethyl, $C_2$-$C_6$, dialkylamino, hydroxyl, or nitro; and -2-furyl, 2-thienyl, 1-naphthyl, 2-naphthyl or 3,4-methylenedioxyphenyl; $R_2$ is selected from the group consisting of —H, —NHC(O)H, —NHC(O)$C_1$-$C_{10}$ alkyl (preferably —NHC(O)$C_4$-$C_6$ alkyl), —NHC(O)phenyl, —NHC(O)phenyl substituted with one, 2, or 3 $C_1$-$C_4$ alkyl, $C_1$-$C_3$ alkoxy, halo, $C_1$-$C_3$ alkylthio, trifluoromethyl, $C_2$-$C_6$ dialkylamino, hydroxy or nitro, —NHC(O)C($CH_3$)=CHCH$_3$, —NHC(O)OC($CH_3$)$_3$, —NHC(O)OCH$_2$ phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$-$C_{10}$ alkyl, —NHC(O)NHC$_1$-$C_{10}$ alkyl, —NHC(O)NHPh, —NHC(O)NHPh substituted with one, 2, or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro, —NHC(O)$C_3$-$C_8$ cycloalkyl, —NHC(O)C(CH$_2$CH$_3$)$_2$CH$_3$, —NHC(O)C(CH$_3$)$_2$CH$_2$Cl, —NHC(O)C(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$, —NHC(O)NHCC(CH$_3$)$_3$ or —NHC(O)NHPh; $R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H; $R_4$ is —H or selected from the group consisting of —OH, —OAc (—OC(O)CH$_3$), —OC(O)OCH$_2$ C(Cl)$_3$, —OCOCH$_2$ CH$_2$ NH$_3^+$ HCOO$^-$, —NHC(O)phenyl, —NHC(O)OC(CH$_3$)$_3$, —OCOCH$_2$ CH$_2$ COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$—), propylene (—$CH_2CH_2CH_2$—), —CH═CH—, 1,2-cyclohexane or 1,2-phenylene, R' is —OH, —OH base, —$NR'_2R'_3$, —$OR'_3$, —$SR'_3$, —$OCH_2C(O)NR'_4R'_5$ where $R'_2$ is —H or —$CH_3$, $R'_3$ is —($CH_2$)—$NR'_6R$) or $(CH_2)_nN^+R'_6R'_7R'_8X^-$ where n is 1-3, $R'_4$ is —H or —$C_1$-$C_4$ alkyl, $R'_5$ is —H. —$C_1$-$C_4$ alkyl, benzyl, hydroxyethyl, —$CH_2CO_2H$ or dimethylaminoethyl, $R'_6$ and $R'_7$ are —$CH_3$, —$CH_2CH_3$, benzyl or $R'_6$ and $R'_7$ together with the nitrogen of $NR'_6R'_7$ form a pyrrolidino, piperidino, morpholino, or N-methylpiperizino group; $R'_8$ is —$CH_3$, —$CH_2CH_3$ or benzyl, $X^-$ is halide, and base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH], —$OC(O)(CH_2)_nNR^2$, $R^3$ [where n is 1-3, $R^2$ is —H or —$C_1$-$C_3$ alkyl and $R^3$ is —H or —$C_1$-$C_3$ alkyl], —OC(O)CH(R")$NH_2$ [where R" is selected from the group consisting of —H, —$CH_3$, —$CH_2$ $CH(CH_3)_2$, —$CH(CH_3)CH_2CH_3$, —$CH(CH_3)_2$, —$CH_2$ phenyl, —$(CH_2)_4NH_2$, —$CH_2CH_2$ COOH, —$(CH_2)_3NHC$ (═NH)$NH_2$], the residue of the amino acid proline, —OC (O)$CH_2CH_2$, —$C(O)CH_2CH_2C(O)NHCH_2CH_2SO_3^-Y^+$, —$OC(O)CH_2CH_2C(O)NHCH_2CH_2CH_2SO_3^-Y^+$ wherein r is $Na^+$ or $N^+(Bu)_4$, —$OC(O)CH_2CH_2C(O)OCH_2CH_2OH$; $R_5$ is —H or —OH, with the overall proviso that when $R_5$ is —OH, $R_4$ is —H and with the further proviso that when $R_5$ is H, $R_4$ is not —H; $R_6$ is —H:—H when $R_7$ is α-$R_{71}$:β-$R_{72}$ where one of $R_{71}$ and $R_{72}$ is —H and the other of $R_{71}$ and $R_{72}$ is —X where X is halo and $R_8$ is —$CH_3$; $R_6$ is —H:—H when $R_7$ is α-H:β-$R_{74}$ where $R_{74}$ and $R_8$ are taken together to form a cyclopropyl ring; $R_{10}$ is —H or —$C(O)CH_3$; and pharmaceutically acceptable salts thereof when the compound contains either an acidic or basic functional group.

Particular paclitaxel analogs include ((azidophenyl)ureido)taxoid, (2α,5α,7β,9α,10β,13α)-5,10,13,20-tetraacetoxytax-11-ene-2,7,9-triol, (2α,5α,9α, 10β)-2,9,10-triacetoxy-5-((β-D-glucopyranosyl)oxy)-3,11-cyclotax-11-en-13-one, 1β-hydroxybaccatin I, 1,7-dihydroxytaxinine, 1-acety-5,7,10-deacetyl-baccatin I, 1-dehydroxybaccatin VI, 1-hydroxy-2-deacetoxy-5-decinnamoyl-taxinine j, 1-hydroxy-7,9-dideacetylbaccatin I, 1-hydroxybaccatin I, 10-acetyl-4-deacetyltaxotere, 10-deacetoxypaclitaxel, 10-Deacetyl baccatin III dimethyl sulfoxide disolvate, 10-deacetyl-10-(3-aminobenzoyl)paclitaxel, 10-deacetyl-10-(7-(diethylamino) coumarin-3-carbonyl)paclitaxel, 10-deacetyl-9-dihydrotaxol, 10-deacetylbaccatine III, 10-deacetylpaclitaxel, 10-deacetylтахіnine, 10-deacetyltaxol, 10-deoxy-10-C-morpholinoethyl docetaxel, 10-O-acetyl-2-O-(cyclohexylcarbonyl)-2-debenzoyltaxotere, 10-O-sec-aminoethyl docetaxel, 11-desmethyllaulimalide, 13-deoxo-13-acetyloxy-7,9-diacetyl-1,2-dideoxytaxine, 13-deoxybaccatin III, 14-hydroxy-10-deacetyl-2-O-debenzoylbacatin III, 14-hydroxy-10-deacetylbaccatin III, 14β-benzoyloxy-13-deacetylbaccatin IV, 14β-benzoyloxy-2-deacetylbaccatin VI, 14β-benzoyloxybaccatin IV, 19-hydroxybaccatin III, 2',2"-methylenedocetaxel, 2',2"-methylenepaclitaxel, 2'-(valylleucyl-lysyl-PABC)paclitaxel, 2'-acetyltaxol, 2'-O-acetyl-7-O—(N-(4'-fluoresceincarbonyl)alanyl)taxol, 2,10,13-triacetoxy-taxa-4(20),11-diene-5,7,9-triol, 2,20-O-diacetyltaxumairol N, 2-(4-azidobenzoyl)taxol, 2-deacetoxytaxinine J, 2-debenzoyl-2-m-methoxybenozyl-7-triethylsilyl-13-oxo-14-hydroxybaccatin III 1,14-carbonate, 2-O-(cyclohexylcarbonyl)-2-debenzoylbaccatin III 13-O—(N-(cyclohexylcarbonyl)-3-cyclohexylisoserinate), 2α,7β,9α,10β,13α-pentaacetoxyltaxa-4 (20), 11-dien-5-ol, 2α,5α,7β,9α,13α-pentahydroxy-10β-acetoxytaxa-4(20),11-diene, 2α,7β,9α,10β,13-pentaacetoxy-11β-hydroxy-5α-(3'-N,N-dimethylamino-3'-phenyl)-propionyloxytaxa-4(20),12-diene, 2α,7β-diacetoxy-5α,10β,13β-trihydroxy-2(3-20) abeotaxa-4(20),11-dien-9-one, 2α,9α-dihydroxy-10β,13α-diacetoxy-5α-(3'-methylamino-3'-phenyl)-propionyloxy-taxa-4(20),11-diene, 2α-hydroxy-7β,9α,10β,13α-tetraacetoxy-5α-(2'-hydroxy-3'-N,N-dimethylamino-3'-phenyl)-propionyloxytaxa-4(20),11-diene, 3'-(4-azidobenzamido) taxol, 3'-N-(4-benzoyldihydrocinnamoyl)-3'-N-debenzoylpaclitaxel, 3'-N-m-aminobenzamido-3'-debenzamidopaclitaxel, 3'-p-hydroxypaclitaxel, 3,11-cyclotaxinine N,N-2,4-deacetyltaxol, 5,13-diacetoxy-taxa-4(20),11-diene-9,10-diol, 5-O-benzoylated taxinine K, 5-O-phenylpropionyloxytaxinine A, 5α,13α-diacetoxy-10β-cinnamoyloxy-4(20),11-taxadien-9α-ol, 6,3'-p-dihydroxypaclitaxel, 6-α-hydroxy-7-deoxy-10-deacetylbaccatin-III, 6-fluoro-10-acetyldocetaxel, 6-hydroxytaxol, 7,13-diacetoxy-5-cinnamyloxy-2(3-20)-abeo-taxa-4(20),11-diene-2, 10-diol, 7,9-dideacetylbaccatin VI, 7-(5'-Biotinylamidopropanoyl)paclitaxel, 7-acetyltaxol, 7-deoxy-10-deacetylbaccatin-III, 7-deoxy-9-dihydropaclitaxel, 7-epipaclitaxel, 7-methylthiomethylpaclitaxel, 7-O-(4-benzoyldihydrocinnamoyl)paclitaxel, 7-O—(N-(4'-fluoresceincarbonyl)alanyl)taxol, 7-xylosyl-10-deacetyltaxol, 8,9-single-epoxy brevifolin, 9-dihydrobaccatin III, 9-dihydrotaxol, 9α-hydroxy-2α,10β,13α-triacetoxy-5α-(3'-N,N-dimethylamino-3'-phenyl)-propionyloxytaxa-4(20),11-diene, baccatin III, baccatin III 13-O—(N-benzoyl-3-cyclohexylisoserinate), BAY59, benzoyltaxol, BMS 181339, BMS 185660, BMS 188797, brevifoliol, butitaxel, cephalomannine, dantaxusin A, dantaxusin B, dantaxusin C, dantaxusin D, dibromo-10-deacetylcephalomannine, DJ927, docetaxel, Flutax 2, glutarylpaclitaxel 6-aminohexanol glucuronide, IDN 5109, IDN 5111, IDN 5127, IDN 5390, isolaulimalide, laulimalide, MST 997, N-(paclitaxel-2'-O-(2-amino)phenyl-propionate)-O—(β-glucuronyl)carbamate, N-(paclitaxel-2'-O-3,3-dimethyl butanoate)-O-(β-glucuronyl)carbamate, N-debenzoyl-N-(3-(dimethylamino)benzoyl)paclitaxel, nonataxel, octreotide-conjugated paclitaxel, Paclitaxel, paclitaxel-transferrin, PNU 166945, poly(ethylene glycol)-conjugated paclitaxel-2'-glycinate, polyglutamic acid-paclitaxel, protax, protaxel, RPR 109881A, SB T-101187, SB T-1102, SB T-1213, SB T-1214, SB T-1250, SB T-12843, tasumatrol E, tasumatrol F, tasumatrol G, taxa-4(20),11(12)-dien-5-yl acetate, taxa-4(20),11(12)-diene-5-ol, taxane, taxchinin N, taxcultine, taxezopidine M, taxezopidine N, taxine, taxinine, taxinine A, taxinine M, taxinine NN-1, taxinine N,N-7, taxol C-7-xylose, taxol-sialyl conjugate, taxumairol A, taxumairol B, taxumairol G, taxumairol H, taxumairol I, taxumairol K, taxumairol M, taxumairol N, taxumairol O, taxumairol U, taxumairol V, taxumairol W, taxumairol-X, taxumairol-Y, taxumairol-Z, taxusin, taxuspinanane A, taxuspinanane B, taxuspine C, taxuspine D, taxuspine F, taxuyunnanine C, taxuyunnanine S, taxuyunnanine T, taxuyunnanine U, taxuyunnanine V, tRA-96023, and wallifoliol. Other paclitaxel analogs include 1-deoxypaclitaxel, 10-deacetoxy-7-deoxypaclitaxel, 10-O-deacetylpaclitaxel 10-monosuccinyl ester, 10-succinyl paclitaxel, 12b-acetyloxy-2a,3,4,4a,5,6,9,10,11, 12,12a,12b-dodecahydro-4,11-dihydroxy-12-(2,5-dimethoxybenzyloxy)-4a,8,13,13-tetramethyl-5-oxo-7,11-methano-1H-cyclodeca(3,4)benz(1,2-b)oxet-9-yl 3-(tert-butyloxycarbonyl)amino-2-hydroxy-5-methyl-4-hexaenoate, 130-nm albumin-bound paclitaxel, 2'-paclitaxel methyl 2-glucopyranosyl succinate, 3'-(4-azidophenyl)-3'-dephenylpaclitaxel, 4-fluoropaclitaxel, 6,6,8-trimethyl-4,4a, 5,6,7,7a,8,9-octahydrocyclopenta(4,5)cyclohepta(1,2-c)-furan-4,8-diol 4-(N-acetyl-3-phenylisoserinate), 6,6,8-trimethyl-4,4a,5,6,7,7a,8,9-octahydrocyclopenta(4,5) cyclohepta(1,2-c)-furan-4,8-diol 4-(N-tert-butoxycarbonyl-3-phenylisoserinate), 7-(3-methyl-3-nitrosothiobutyryl) paclitaxel, 7-deoxypaclitaxel, 7-succinylpaclitaxel, A-Z-

CINN 310, AI-850, albumin-bound paclitaxel, AZ 10992, isotaxel, MAC321, MBT-0206, NK105, Pacliex, paclitaxel poliglumex, paclitaxel-EC-1 conjugate, polilactofate, and TXD 258. Other paclitaxel analogs are described in U.S. Pat. Nos. 4,814,470, 4,857,653, 4,942,184, 4,924,011, 4,924,012, 4,960,790; 5,015,744; 5,157,049; 5,059,699; 5,136,060; 4,876,399; and 5,227,400

Other Hydrophobic Agents

Other hydrophobic agents include analgesics and antiinflammatory agents (e.g., aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac), antihelmintics (e.g., albendazole, bephenium hydroxynaphthoate, cambendazole, dichlorophen, ivermectin, mebendazole, oxamniquine, oxfendazole, oxantel embonate, praziquantel, pyrantel embonate, thiabendazole), anti-arrhythmic agents (e.g., amiodarone HCl, disopyramide, flecamide acetate, quinidine sulphate, anti-bacterial agents (e.g., benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim), anti-coagulants (e.g., dicoumarol, dipyridamole, nicoumalone, phenindione), antidepressants (e.g., amoxapine, maprotiline HCl, mianserin HCl, nortriptyline HCl, trazodone HCl, trimipramine maleate), antidiabetics (e.g., acetohexamide, chlorpropamide, glibenclamide, gliclazide, glipizide, tolazamide, tolbutamide), anti-epileptics (e.g., beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid), antifungal agents (e.g., amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid), antigout agents (e.g., allopurinol, probenecid, sulphin-pyrazone), antihypertensive agents (e.g., amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCl, reserpine, terazosin HCl), antimalarials (e.g., amodiaquine, chloroquine, chlorproguanil HCl, halofantrine HCl, mefloquine HCl, proguanil HCl, pyrimethamine, quinine sulphate), antimigraine agents (e.g., dihydroergotamine mesylate, ergotamine tartrate, methysergide maleate, pizotifen maleate, sumatriptan succinate), anti-muscarinic agents (e.g., atropine, benzhexol HCl, biperiden, ethopropazine HCl, hyoscyamine, mepenzolate bromide, oxyphencylcimine HCl, tropicamide), anti-neoplastic agents and immunosuppressants (e.g., aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone), anti-protazoal agents (e.g., benznidazole, clioquinol, decoquinate, diiodohydroxyquinoline, diloxanide furoate, dinitolmide, furzolidone, metronidazole, nimorazole, nitrofurazone, ornidazole, tinidazole), anti-thyroid agents (e.g., carbimazole, propylthiouracil), anxiolytic, sedatives, hypnotics and neuroleptics (e.g., alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone), β-Blockers (e.g., acebutolol, alprenolol, atenolol, labetalol, metoprolol, nadolol, oxprenolol, pindolol, propranolol), cardiac inotropic agents (e.g., amrinone, digitoxin, digoxin, enoximone, lanatoside C, medigoxin), corticosteroids (e.g., beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone), diuretics: acetazolamide, amiloride, bendrofluazide, bumetanide, chlorothiazide, chlorthalidone, ethacrynic acid, frusemide, metolazone, spironolactone, triamterene), anti-parkinsonian agents (e.g., bromocriptine mesylate, lysuride maleate), gastrointestinal agents (e.g., bisacodyl, cimetidine, cisapride, diphenoxylate HCl, domperidone, famotidine, loperamide, mesalazine, nizatidine, omeprazole, ondansetron HCl, ranitidine HCl, sulphasalazine), histamine H, -receptor antagonists (e.g., acrivastine, astemizole, cinnarizine, cyclizine, cyproheptadine HCl, dimenhydrinate, flunarizine HCl, loratadine, meclozine HCl, oxatomide, terfenadine), lipid regulating agents (e.g., bezafibrate, clofibrate, fenofibrate, gemfibrozil, probucol), nitrates and other anti-anginal agents (e.g., amyl nitrate, glyceryl trinitrate, isosorbide dinitrate, isosorbide mononitrate, pentaerythritol tetranitrate), opioid analgesics (e.g., codeine, dextropropyoxyphene, diamorphine, dihydrocodeine, meptazinol, methadone, morphine, nalbuphine, pentazocine), sex hormones (e.g., clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone), and stimulants (e.g., amphetamine, dexamphetamine, dexfenfluramine, fenfluramine, mazindol).

Polypeptide Conjugates

Conjugates including an active agent a polypeptide may be used in the formulation described herein. As described in U.S. Patent Applications Publication Nos. 2006/0182684, and 2006/0189515, and U.S. Provisional Application No. 61/008, 880, filed Dec. 20, 2007, we have developed polypeptide-agent conjugates. Such conjugates may include any polypeptide described herein, a hydrophobic agent such as paclitaxel or a paclitaxel analog (e.g., those described herein), and a linker (e.g., those described herein). Paclitaxel conjugates are exemplified by ANG1005, which includes the AngioPep-2 peptide (SEQ ID NO:97) conjugated to three paclitaxel molecules through ester linkages at the N-terminus, an through lysines at positions 10 and 15. The structure of ANG1005 is

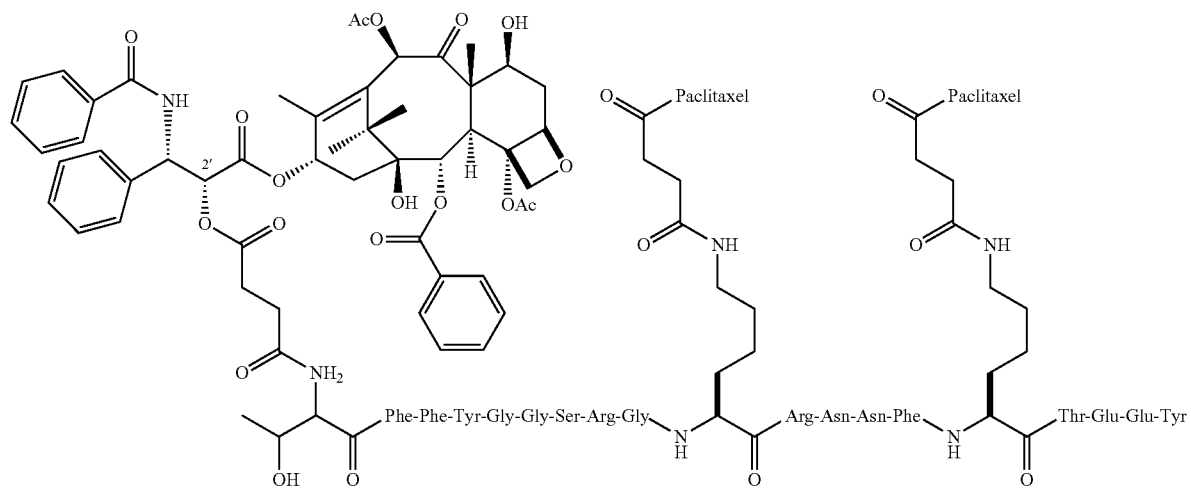

The conjugates, in certain embodiments, can cross the blood-brain barrier (BBB) or can be preferentially targeted to certain cell types, such as liver, lung, kidney, muscle cells or may be targeted to tumor cells (of any cell type described herein). These agents conjugated to these peptides can exhibit increased uptake into the targeted cells, for example, by receptor-mediated endocytosis (e.g., through an LRP receptor). The conjugated agents may, either alternatively or in addition, exhibit increased stability or reduced expulsion from the cell (e.g., due to P-glycoprotein mediated efflux).

Polypeptides

The compositions and methods of the invention may include any polypeptide described herein, for example, any of the polypeptides described in Table 10 (e.g., a polypeptide defined in any of SEQ ID NOS:1-105 and 107-112 such as SEQ ID NOS:1-97, 99, 100, 101, or 107-112), or any fragment, analog, derivative, or variant thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The invention can also feature fragments of these polypeptides (e.g., a functional fragment). In certain embodiments, the fragments are capable of entering or accumulating in a particular cell type (e.g., liver, lung, kidney, spleen, or muscle) or capable of crossing the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides may be identified by using one of the assays or methods described in U.S. Patent Application Publication No. 2006/0189515, which is hereby incorporated by reference, or by any method known in the art. For example, a candidate vector may be produced by conventional polypeptide synthesis, conjugated with Taxol and administered to a laboratory animal. A biologically active vector may be identified, for example, based on its efficacy to increase survival of an animal injected with tumor cells and treated with the conjugate as compared to a control which has not been treated with a conjugate (e.g., treated with the unconjugated agent).

In another example, a biologically active polypeptide may be identified based on its location in the parenchyma in an in situ cerebral perfusion assay. In vitro BBB assays, such as the model developed by CELLIAL™ Technologies, may be used to identify such vectors.

Assays to determine accumulation in other tissues may be performed as well. Labeled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labeled with a radioactive isotope (e.g., $^{125}$I). The polypeptide is then administered to an animal. After a period of time, the animal is sacrificed, and the animal's organs are extracted. The amount of radioisotope in each organ can then be measured using any means known in the art. By comparing the amount of a labeled candidate polypeptide in a particular organ without amount of labeled control, the ability of the candidate polypeptide the rate or amount of accumulation of a candidate polypeptide in a particular tissue can be ascertained. Appropriate negative controls include any polypeptide known not be transported into a particular cell type.

TABLE 10

| SEQ ID NO: | |
|---|---|
| 1 | T F V Y G G C R A K R N N F K S A E D |
| 2 | T F Q Y G G C M G N G N N F V T E K E |
| 3 | P F F Y G G C G G N R N N F D T E E Y |
| 4 | S F Y Y G G C L G N K N N Y L R E E E |
| 5 | T F F Y G G C R A K R N N F K R A K Y |
| 6 | T F F Y G G C R G K R N N F K R A K Y |

TABLE 10-continued

| SEQ ID NO: | Sequence |
|---|---|
| 7 | T F F Y G G C R A K K N N Y K R A K Y |
| 8 | T F F Y G G C R G K K N N F K R A K Y |
| 9 | T F Q Y G G C R A K R N N F K R A K Y |
| 10 | T F Q Y G G C R G K K N N F K R A K Y |
| 11 | T F F Y G G C L G K R N N F K R A K Y |
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |

TABLE 10-continued

| SEQ ID NO: | |
|---|---|
| 83 | T F F Y G G C L G N R N N F K T E E Y |
| 84 | T F F Y G C G R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |

TABLE 10-continued

| SEQ ID NO: | |
|---|---|
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R T E E Y |
| 116 | T F F Y G G S R G R R N N F R T E E Y C |

Peptide no. 5 includes the sequence of SEQ ID NO: 5 and is amidated at its C-terminus (see for example FIG. 1)
Peptide No. 67 includes the sequence of SEQ ID NO: 67 and is amidated at its C-terminus (see for example FIG. 1)
Peptide No. 76 includes the sequence of SEQ ID NO: 76 and is amidated at its C-terminus (see for example FIG. 1).
Peptide no. 91 includes the sequence of SEQ ID NO: 91 and is amidated at its C-terminus (see for example FIG. 1).
Peptide No. 107 includes the sequence of SEQ ID NO: 97 and is acetylated at its N-terminus.
Peptide No. 109 includes the sequence of SEQ ID NO: 109 and is acetylated at its N-terminus.
Peptide No. 110 includes the sequence of SEQ ID NO: 110 and is acetylated at its N-terminus.

The amine groups of Angiopep-1 (SEQ ID NO:67) and Angiopep-2 (SEQ ID NO:97) have been used as sites for conjugation of agents. To study the role of amine groups in conjugation and their impact in the overall transport capacity of these vectors, new vectors, based on the Angiopep-1 and Angiopep-2 sequence, were designed with variable reactive amine groups and variable overall charge. These polypeptides are shown in Table 11.

TABLE 11

Vectors with variable amine group targets

| Polypeptide Name | Polypeptide Sequences | Reactive amines (positions) | Charge | SEQ ID No. |
|---|---|---|---|---|
| Angiopep-3* | Ac[1]-TFFYGGSRGKRNNFKTEEY | 2 (10, 15) | +1 | 107 |
| Angiopep-4b | RFFYGGSRGKRNNFKTEEY | 3 (1, 10, 15) | +3 | 108 |
| Angiopep-4a | Ac[1]-RFFYGGSRGKRNNFKTEEY | 2 (10, 15) | +2 | 109 |
| Angiopep-5 | Ac[1]-RFFYGGSRGKRNNFRTEEY | 1 (10) | +2 | 110 |
| Angiopep-6 | TFFYGGSRGKRNNFRTEEY | 2 (1, 10) | +2 | 111 |
| Angiopep-7 | TFFYGGSRGRRNNFRTEEY | 1 (1) | +2 | 112 |

*Angiopep-3 is an acetylated form of Angiopep-2.
[1]Ac represents acetylation.

Modified Polypeptides

The compositions and methods of the invention may also include a polypeptide having a modification of an amino acid sequence described herein (e.g., polypeptide having a sequence described in any one of SEQ ID NOS:1-105 and 107-116 such as AngioPep-3, -4a, -4b, -5, -6, or -7). In certain embodiments, the modification does not destroy significantly a desired biological activity. In some embodiments, the modification may cause a reduction in biological activity (e.g., by at least 5%, 10%, 20%, 25%, 35%, 50%, 60%, 70%, 75%, 80%, 90%, or 95%). In other embodiments, the modification has no effect on the biological activity or may increase (e.g., by at least 5%, 10%, 25%, 50%, 100%, 200%, 500%, or 1000%) the biological activity of the original polypeptide. The modified polypeptide may have or may optimize one or more of the characteristics of a polypeptide of the invention which, in some instance might be needed or desirable. Such characteristics include in vivo stability, bioavailability, toxicity, immunological activity, or immunological identity.

Polypeptides used in the invention may include amino acids or sequences modified either by natural processes, such as posttranslational processing, or by chemical modification techniques known in the art. Modifications may occur anywhere in a polypeptide including the polypeptide backbone, the amino acid side-chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide may further include an amino acid insertion, deletion, or substitution, either conservative or nonconservative (e.g., D-amino acids, desamino acids) in the polypeptide sequence (e.g., where such changes do not substantially alter the biological activity of the polypeptide).

Substitutions may be conservative (i.e., wherein a residue is replaced by another of the same general type or group) or non-conservative (i.e., wherein a residue is replaced by an amino acid of another type). In addition, a non-naturally occurring amino acid may substituted for a naturally occurring amino acid (i.e., non-naturally occurring conservative amino acid substitution or a non-naturally occurring non-conservative amino acid substitution).

Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogues may be generated by substitutional mutagenesis and retain the biological activity of the original polypeptide. Examples of substitutions identified as "conservative substitutions" are shown in Table 12. If such substitutions result in a change not desired, then other type of substitutions, denominated "exemplary substitutions" in Table 12, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe), (2) neutral hydrophilic: Cysteine (Cys), Serine (Ser), Threonine (Thr)

(3) acidic/negatively charged: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro);

(6) aromatic: Tryptophan (Trp), Tyrosine (Tyr), Phenylalanine (Phe), Histidine (His), (7) polar: Ser, Thr, Asn, Gln (8) basic positively charged: Arg, Lys, His, and;

(9) charged: Asp, Glu, Arg, Lys, His

Other conservative amino acid substitutions are listed in Table 3.

TABLE 12

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |

TABLE 12-continued

Amino acid substitution

| Original residue | Exemplary substitution | Conservative substitution |
|---|---|---|
| Tyr (Y) | Trp, Phe, Thr, Ser | Phe |
| Val (V) | Ile, Leu, Met, Phe, Ala, norleucine | Leu |

Additional Analogues

The polypeptides and conjugates used in the invention may include polypeptide analogs of aprotinin known in the art. For example, U.S. Pat. No. 5,807,980 describes Bovine Pancreatic Trypsin Inhibitor (aprotinin)-derived inhibitors as well as a method for their preparation and therapeutic use including the polypeptide of SEQ ID NO:102. These polypeptides have been used for the treatment of a condition characterized by an abnormal appearance or amount of tissue factor and/or factor VIIIa such as abnormal thrombosis. U.S. Pat. No. 5,780,265 describes serine protease inhibitors capable of inhibiting plasma kallikrein, including SEQ ID NO:103. U.S. Pat. No. 5,118,668 describes Bovine Pancreatic Trypsin Inhibitor variants, including SEQ ID NO:105. The aprotinin amino acid sequence (SEQ ID NO:98), the Angiopep-1 amino acid sequence (SEQ ID NO:67), and SEQ ID NO:104, as well as some sequences of biologically active analogs may be found in International Application Publication No WO 2004/060403.

An exemplary nucleotide sequence encoding an aprotinin analogue is illustrated in SEQ ID NO:106 (atgagaccag atttct- gcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggt- gcttag; Genbank accession No X04666). This sequence encodes a lysine at position 16 instead of a valine, as found in SEQ ID NO:98. A mutation in the nucleotide sequence of SEQ ID NO:106 may be introduced by methods known in the art to change the produce the polypeptide of SEQ ID NO:98 having a valine in position 16. Additional mutations or fragments may be obtained using any technique known in the art.

Other examples of aprotinin analogs may be found by performing a protein BLAST (Genebank: www.ncbi.nlm.nih.gov/BLAST/) using the synthetic aprotinin sequence (or portion thereof) disclosed in International Application No. PCT/CA2004/000011. Exemplary aprotinin analogs are found under accession Nos. CAA37967 (GI:58005) and 1405218C (GI:3604747).

Preparation of Polypeptide Derivatives and Peptidomimetics

In addition to polypeptides consisting only of naturally occurring amino acids, peptidomimetics or polypeptide analogs can also be used in the present invention. Polypeptide analogs are commonly used in the pharmaceutical industry as non-polypeptide drugs with properties analogous to those of the template polypeptide. The non-polypeptide compounds are termed "polypeptide mimetics" or peptidomimetics (Fauchere et al., *Infect. Immun.* 54:283-287, 1986; Evans et al., *J. Med. Chem.* 30:1229-1239, 1987). Polypeptide mimetics that are structurally related to therapeutically useful polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH═CH—(cis and trans), —CH$_2$SO—, —CH(OH)CH$_2$—, —COCH$_2$— etc., by methods well known in the art (Spatola, *Peptide Backbone Modifications, Vega Data*, 1(3):267, 1983); Spatola et al. (*Life Sci.* 38:1243-1249, 1986); Hudson et al. (*Int. J. Pept. Res.* 14:177-185, 1979); and Weinstein. B., 1983, Chemistry and Biochemistry, of Amino Acids, Peptides and Proteins, Weinstein eds, Marcel Dekker, New-York). Such polypeptide mimetics may have significant advantages over naturally-occurring polypeptides including more economical production, greater chemical stability, enhanced pharmacological properties (e.g., half-life, absorption, potency, efficiency), reduced antigenicity and others.

While the polypeptides used in the invention may be effective in entering particular cell types (e.g., those described herein), their effectiveness may be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the polypeptide and require a free N-terminus (Powell of al., *Pharm. Res.* 10:1268-1273, 1993). In light of this, it is often advantageous to use modified versions of polypeptides. The modified polypeptides retain the structural characteristics of the original L-amino acid polypeptides that confer biological activity with regard to IGF-1, but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable polypeptides. Thus, a polypeptide derivative or peptidomimetic used in the present invention may be all L, all D or mixed D, L polypeptide. The presence of an N-terminal or C-terminal D-amino acid increases the in vivo stability of a polypeptide because peptidases cannot utilize a D-amino acid as a substrate (Powell et al., *Pharm. Res.* 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, Nature 368:692-693, 1994; Jameson et al., *Nature* 368:744-746, 1994). In addition to reverse-D-polypeptides, constrained polypeptides comprising a consensus sequence or a substantially identical consensus sequence variation may be generated by methods well known in the art (Rizo and Gierasch, *Ann. Rev. Biochem.* 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at peptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., *J. Pharm. Pharmacol.* 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the compositions and methods of the present invention can include modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides used in the invention are also encompassed. Such longer polypeptide sequences would be expected to have the same biological activity (e.g., entering particular cell types) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptide or derivative.

Other derivatives that can be used in present invention are dual polypeptides consisting of two of the same, or two different polypeptides described herein covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides used in the present invention consist of polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids of a polypeptide used in the present invention and desirably has a functional activity equivalent or greater than a polypeptide used in the invention.

Polypeptide derivatives used in the present invention can be made by altering the amino acid sequences by substitution, addition, or deletion or an amino acid residue to provide a functionally equivalent molecule, or functionally enhanced or diminished molecule, as desired. The derivatives used in the present invention include, but are not limited to, those containing, as primary amino acid sequence, all or part of the amino acid sequence of the polypeptides described herein (e.g., any one of SEQ ID NOS:1-105 and 107-116) including altered sequences containing substitutions of functionally equivalent amino acid residues. For example, one or more amino acid residues within the sequence can be substituted by another amino acid of a similar polarity which acts as a functional equivalent, resulting in a silent alteration. Substitution for an amino acid within the sequence may be selected from other members of the class to which the amino acid belongs. For example, the positively charged (basic) amino acids include, arginine, lysine and histidine. The nonpolar (hydrophobic) amino acids include, leucine, isoleucine, alanine, phenylalanine, valine, proline, tryptophan and methionine. The uncharged polar amino acids include serine, threonine, cysteine, tyrosine, asparagine and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

Assays to Identify Peptidomimetics

As described above, non-peptidyl compounds generated to replicate the backbone geometry and pharmacophore display (peptidomimetics) of the polypeptides identified by the methods can possess attributes of greater metabolic stability, higher potency, longer duration of action and better bioavailability.

The peptidomimetics compounds used in the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al., *J. Med. Chem.* 37:2678, 1994); Cho et al. (*Science* 261:1303, 1993); Carell et al. (*Angew. Chem, Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide that can be used the present invention is identified, it may be isolated and purified by any number of standard methods including, but not limited to, differential solubility (e.g., precipitation), centrifugation, chromatography (e.g., affinity, ion exchange, size exclusion, and the like) or by any other standard techniques used for the purification of polypeptides, peptidomimetics or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds used in the present invention may be obtained using the following three-phase process: (1) scanning the polypeptides used in the present invention to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best polypeptide candidates. These and related platforms (reviewed in Halab et al., *Biopolymers* 55:101-122, 2000; and Hanessian et al. *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native polypeptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics, or other small molecules used in the present invention may be used to refine and prepare analogous molecular structures having similar or better properties. Accordingly, the compounds used in the present invention also include molecules that share the structure, polarity, charge characteristics and side chain properties of the polypeptides described herein.

In summary, based on the disclosure herein, those skilled in the art can develop polypeptides and peptidomimetics screening assays which are useful for identifying compounds for targeting an agent to particular cell types (e.g., those described herein). The assays may be developed for low-throughput, high-throughput, or ultra-high throughput screening formats. Assays of the present invention include assays which are amenable to automation.

Conjugates

The polypeptides described herein or derivatives thereof may be linked to an agent. For example, the polypeptide (e.g., any described herein) may be attached to a therapeutic agent, a diagnostic agent, or to a label. In certain embodiments, the polypeptide is linked to or labeled with a detectable label, such as a radioimaging agent, for diagnosis of a disease or condition. Examples of these agents include a radioimaging agent-antibody-vector conjugate, where the antibody binds to a disease or condition-specific antigen (e.g., for diagnosis or therapy). Other binding molecules are also contemplated by the invention. In other cases, the polypeptide or derivative is linked to a therapeutic agent, to treat a disease or condition, or may be linked to or labeled with mixtures thereof. The disease or condition may be treated by administering a vector-agent conjugate to an individual under conditions which allow transport of the agent across the BBB or into a particular cell type. Each polypeptide may include at least 1, 2, 3, 4, 5, 6, or 7 agents. In other embodiments, each agent has at least 1, 2, 3, 4, 5, 6, 7, 10, 15, 20, or more polypeptides attached thereto. The conjugates of the invention may be able to promote accumulation (e.g., due to increased uptake or reduced removal) of the agent in a particular cell type or tissue such as liver, lung, kidney, spleen or muscle of a subject.

The agent may be releasable from the vector after transport into a particular cell type or across the BBB. The agent can be released, for example, by enzymatic cleavage or other breakage of a chemical bond between the vector and the agent. The released agent may then function in its intended capacity in the absence of the vector.

Therapeutic Agents.

A therapeutic agent may be any biologically active agent. For example, a therapeutic may be a drug, a medicine, an agent emitting radiation, a cellular toxin (for example, a chemotherapeutic agent), a biologically active fragment thereof, or a mixture thereof to treat a disease (e.g., to killing cancer cells) or it may be an agent to treat a disease or condition in an individual. A therapeutic agent may be a synthetic product or a product of fungal, bacterial or other microorganism (e.g., mycoplasma or virus), animal, such as reptile, or plant origin. A therapeutic agent and/or biologically active fragment thereof may be an enzymatically active agent and/or fragment thereof, or may act by inhibiting or blocking an important and/or essential cellular pathway or by competing with an important and/or essential naturally occurring cellular component. Other therapeutic agents include antibodies and antibody fragments.

Anticancer Agents.

Any anticancer agent known in the art may be part of a conjugate used in the invention. In certain embodiments, the agent is paclitaxel or a paclitaxel analog (e.g., those described herein). Cancers of the brain may be treated with a conjugate containing a vector that is efficiently transported across the BBB (e.g., AngioPep-1, AngioPep-2, AngioPep-3, Angio- Pep-4a, AngioPep-4b, AngioPep-5, or AngioPep-6). Liver, lung, kidney, or spleen cancers may be treated with an anticancer agent conjugated to a vector that is transported efficiently into the appropriate cell type (e.g., AngioPep-7). Exemplary agents include abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, Denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumutnab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid.

Detectable Labels.

For the purpose of detection or diagnosis, the conjugate used in the invention may be labeled. Detectable labels, or markers, may be a radiolabel, a fluorescent label, a nuclear magnetic resonance active label, a luminescent label, a chromophore label, a positron emitting isotope for PET scanner, chemiluminescence label, or an enzymatic label. Exemplary radioimaging agents emitting radiation (detectable radiolabels) include indium-111, technitium-99, or low dose iodine-131. Gamma and beta emitting radionuclides include $^{67}$Cu, $^{67}$Ga, $^{90}$Y, $^{111}$In, $^{99m}$Tc, and $^{201}$Tl). Positron emitting radionuclides include $^{18}$F, $^{55}$Co, $^{60}$Cu, $^{62}$Cu, $^{64}$Cu, $^{66}$Ga, $^{68}$Ga, $^{82}$Rb, and $^{86}$Y. Fluorescent labels include Cy5.5, Alexa 488, green fluorescent protein (GFP), fluorescein, and rhodamine. Chemiluminescence labels include luciferase and β-galactosidase. Enzymatic labels include peroxidase and phosphatase. A histag may also be a detectable label. For example, conjugates may include a vector moiety and an antibody moiety (antibody or antibody fragment), which may further include a label. In this case, the label may be attached to either the vector or to the antibody.

Antibodies.

Antibodies may also be part of a conjugate used in the invention. The conjugation by accomplished using any means known in the art (e.g., using the conjugation strategies described herein). Any diagnostic or therapeutic antibody may be conjugated to one or more (e.g., 2, 3, 4, 5, 6, 7, 8, 9, 10, or more) vectors of the invention. In addition, antibody fragments (e.g., capable of binding to an antigen) may also be conjugated to the vectors of the invention. Antibody fragments include the Fab and Fc regions, heavy chain, and light chain of an antibody (e.g., of any antibody described herein). Exemplary antibodies for use in diagnosis and therapy of cancer include ABX-EGF (Panitimumab), OvaRex (Oregovemab), Theragyn (pemtumomabytrrium-90), Therex, Bivatuzumab, Panorex (Edrecolomab), ReoPro (Abciximab), Bexxar (Tositumomab), MAb, idiotypic 105AD7, Anti-Ep-CAM (Catumaxomab), MAb lung cancer (from Cytoclonal), Herceptin (Trastuzumab), Rituxan (Rituximab), Avastin (Bevacizumab) AMD Fab (Ranibizumab), E-26 ($2^{nd}$ gen. IgE) (Omalizumab), Zevalin (Rituxan+yttrium-90) (Ibriturnomab tiuxetan), Cetuximab, BEC2 (Mitumomab), IMC-1C11, nuC242-DM1, LymphoCide (Epratuzumab), LymphoCide Y-90, CEA-Cide (Labetuzumab), CEA-Cide Y-90, CEA-Scan (Tc-99m-labeled arcitumomab), LeukoScan (Tc-99m-labeled sulesomab), LymphoScan (Tc-99m-labeled bectumomab), AFP-Scan (Tc-99m-labeled), HumaRAD-HN (+yttrium-90), HumaSPECT (Votumumab), MDX-101 (CTLA-4), MDX-210 (her-2 overexpression), MDX-210/MAK, Vitaxin, MAb 425, IS-IL-2, Campath (alemtuzumab), CD20 streptavidin, Avidicin, (albumin+NRLU13), Oncolym (+iodine-131) Cotara (+iodine-131), C215 (+staphylococcal enterotoxin, MAb lung/kidney cancer (from Pharmacia Corp.), nacolomab tafenatox (C242 staphylococcal enterotoxin), Nuvion (Visilizumab), SMART M195, SMART 1D10, CEAVac, TriGem, TriAb, NovoMAb-G2 radiolabeled, Monopharm C, GlioMAb-H (+gelonin toxin), Rituxan (Rituximab), and ING-1. Additional therapeutic antibodies include 5G1.1 (Ecluizumab), 5G1.1-SC (Pexelizumab), ABX-CBL (Gavilimomab), ABX-IL8, Antegren (Natalizumab), Anti-CD11a (Efalizumab), Anti-CD18 (from Genetech), Anti-LFA1, Antova, BTI-322, CDP571, CDP850, Corsevin M, D2E7 (Adalimumab), Humira (Adalimumab), Hu23F2G (Rovelizumab), IC14, IDEC-114, IDEC-131, IDEC-151, IDEC-152, Infliximab (Remicade), LDP-01, LDP-02, MAK-195F (Afelimomab), MDX-33, MDX-CD4, MEDI-507 (Siplizumab), OKT4A, OKT3 (Muromonab-CD3), and ReoPro (Abciximab).

Conjugation Linkers

The conjugate (e.g., a polypeptide-agent conjugate) may be obtained using any cross-linking (conjugation) reagent or protocol know in the art, many of which are commercially available. Such protocols and reagents include, cross-linkers reactive with amino, carboxyl, sulfhydryl, carbonyl, carbohydrate and/or phenol groups. The amounts, times, and conditions of such protocols can be varied to optimize conjugation. Cross-linking reagents contain at least two reactive groups and are generally divided into homofunctional cross-linkers (containing identical reactive groups) and heterofunctional cross-linkers (containing non-identical reactive groups). The cross-linkers of the invention may be either homobifunctional and/or heterobifunctional. Furthermore the cross-linker may incorporate a 'spacer' between the reactive moieties, or the two reactive moieties in the cross-linker may be directly linked. Bonds may include ester bonds.

Figure 2:
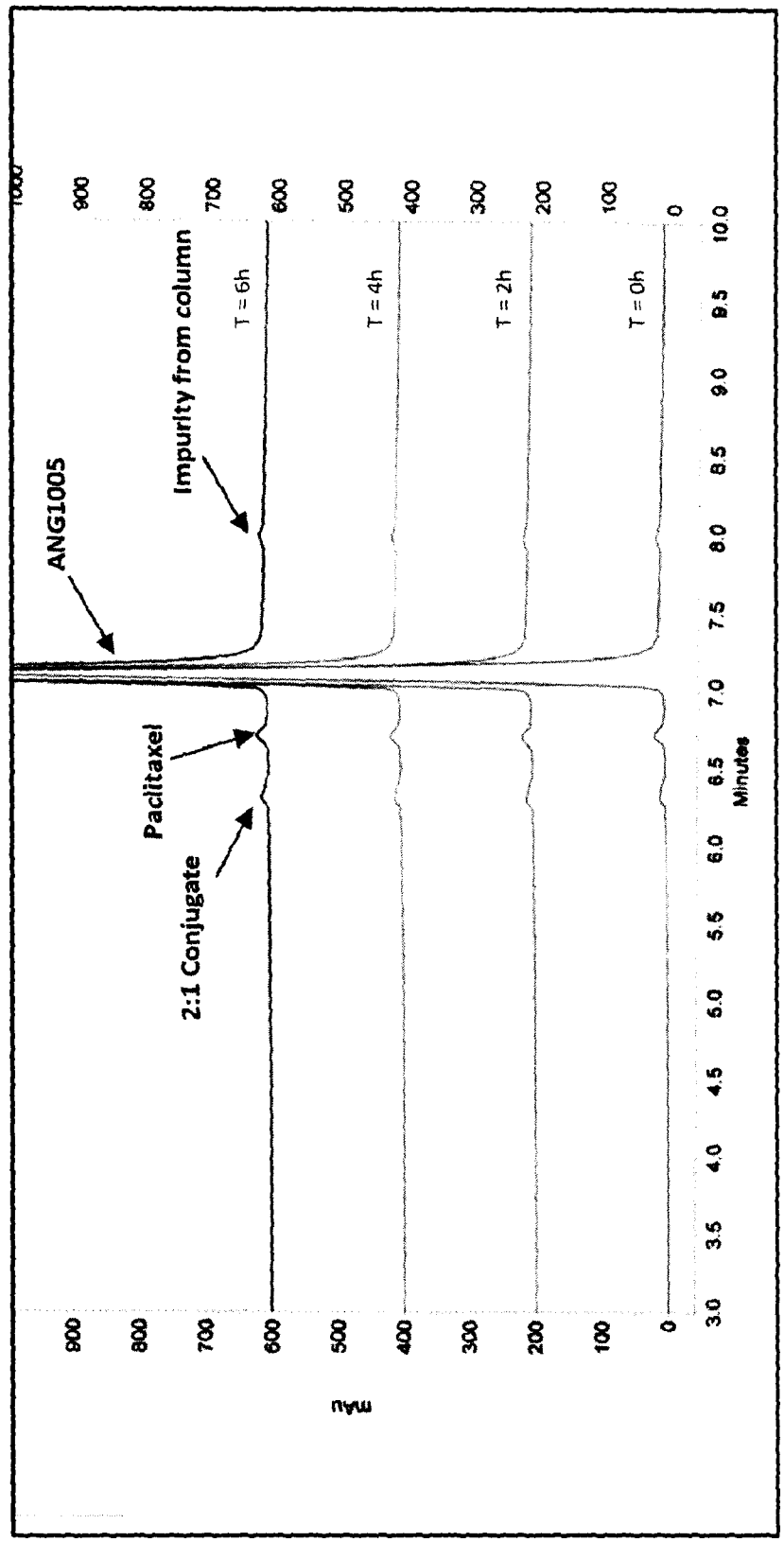
FIG. 2 is a graph showing HPLC profiles of reconstituted ANG1005 for Injection diluted in D5W to 1.0 mg/ml under conditions of clinical use overtime.

Exemplary linkers include BS$^3$ [Bis(sulfosuccinimidyl) suberate], NHS/EDC (N-hydroxysuccinimide and N-ethyl-(dimethylaminopropyl)carbodimide, Sulfo-EMCS ([N-e-Maleimidocaproic acid]hydrazide), SATA (N-succinimidyl-5-acetylthioacetate), and hydrazide. BS$^3$ is a homobifunctional N-hydroxysuccinimide ester that targets accessible primary amines. A conjugation scheme is exemplified in FIG. 2. NHS/EDC allows for the conjugation of primary amine groups with carboxyl groups. Sulfo-EMCS are heterobifunctional reactive groups (maleimide and NHS-ester) that are reactive toward sulfhydryl and amino groups. Amine coupling using sulfo-NHS/EDC activation may be used to cross-link therapeutic antibodies with the polypeptides of the invention, as exemplified in FIGS. 3 and 4. This is a fast, simple and reproducible coupling technique. The resulting conjugate is stable and retains the biological activity of the antibody. Moreover, it has a high conjugation capacity that can be reliably controlled and a low non-specific interaction during coupling procedures. SATA is reactive towards amines and adds protected sulfhydryls groups. The NHS-ester reacts with primary amines to form stable amide bonds. Sulfhydryl groups may be deprotected using hydroxylamine. This conjugation method is exemplified in FIG. 5. Hydrazide can be used to link carboxyl groups to primary amines, as shown in FIG. 6, and may therefore be useful for linking glycoproteins. Additional exemplary linkers are illustrated in FIG. 7.

Small molecules such as therapeutic agents can be conjugated to polypeptides (e.g., those described herein). The exemplary small molecule, paclitaxel, has two strategic positions (position C2' and C7) useful for conjugation. Conjugation of a vector or vector of the invention to paclitaxel can be performed as follows (FIG. 8). Briefly, paclitaxel is reacted with anhydride succinic pyridine for three hours at room temperature to attach a succinyl group in position 2'. The 2'-succinyl paclitaxel has a cleavable ester bond in position 2' can simply release succinic acid. This cleavable ester bond can be further used for various modifications with linkers, if desired. The resulting 2'-O-succinyl-paclitaxel is then reacted with EDC/NHS in DMSO for nine hours at room temperature, followed by the addition of the vector or vector in Ringer/DMSO for an additional reaction time of four hours at room temperature. The reaction of conjugation depicted in FIG. 8 is monitored by HPLC. Each intermediate, such as paclitaxel, 2'-O-succinyl-paclitaxel and 2'-O—NHS-succinyl-paclitaxel, is purified and validated using different approaches such as HPLC, thin liquid chromatography, NMR ($^{13}$C or $^1$H exchange), melting point, mass spectrometry. The final conjugate is analyzed by mass spectrometry and SDS-polyacrylamide gel electrophoresis. This allows determining the number of paclitaxel molecules conjugated on each vector.

Pharmaceutical Compositions

Because hydrophobic agents often exhibit limited solubility in aqueous solution, pharmaceutical compositions of the inventions may include solubilizing agents. Our exemplary formulations of ANG1005 include DMSO and SOLUTOL® HS 15, however, other solubilizing agents, either in place of or in addition to these agents may be useful in the compositions of the invention. The compositions may further include buffering agents, tonicity agents, and lyophilization agents (e.g., bulking or cryoprotectant agents).

Solubilizing Agents

The compositions and methods of the invention may include any solubilizing agent known in the art. Such agents may make up at least 1%, 2%, 5%, 10%, 15%, 20%, 25%, 30%, 35%, 40%, 50%, 60%, or 70% of the mass of the composition. Exemplary solubilizers include water-soluble organic solvents (e.g., polyethylene glycol 300, polyethylene glycol 400, ethanol, propylene glycol, glycerin, N-methyl-2-pyrrolidone, dimethylacetamide, and dimethylsulfoxide), non-ionic surfactants (e.g., CREMOPHOR® EL, CREMOPHOR® RH 40, CREMOPHOR® RH 60, d-α-tocopherol polyethylene glycol 1000 succinate, polysorbate 20, polysorbate 80, SOLUTOL® HS 15 (Macrogol 15 Hydroxystearate), sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750), water-insoluble lipids (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil), organic liquids/semi-solids (beeswax, d-α-tocopherol, oleic acid, medium-chain mono- and diglycerides), cyclodextrins (e.g., α-cyclodextrin, β-cyclodextrin, hydroxypropyl-β-cyclodextrin, and sulfobutylether-β-cyclodextrin), and phospholipids (e.g., hydrogenated soy phosphatidylcholine, distearoylphosphatidylglycerol, 1-α-dimyristoylphosphatidylcholine, 1-α-dimyristoylphosphatidylglycerol).

Buffering Agents

The compositions and methods of the invention may also include one or more buffering agents. Depending on the hydrophobic agent, it may be desirable to maintain the pH or tonicity of the pharmaceutical composition (e.g., to minimize degradation of the active agent or to maximize safety or efficacy of the agent when used in treatment). Buffering to any particular pH or range of pH may be accomplished using the appropriate buffer (e.g., to pH 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, or any range between these values). The buffer may present at any strength necessary to achieve the desired buffering effect (e.g., 1 mM, 10 mM, 20 mM, 50 mM, 100 mM, 200 mM, 500 mM, 1.0 M, 1.5 M, or any range between these values). Exemplary buffering agents include citric acid/phosphate, acetate, barbital, borate, Britton-Robinson, cacodylate, citrate, collidine, formate, maleat, Mcllvaine, phosphate, Prideaux-Ward, succinate, citrate-phosphate-borate (Teorell-Stanhagen), veronal acetate, MES (2-(N-morpholino) ethanesulfonic acid), BIS-TRIS (bis(2-hydroxyethyl)iminotris-(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxy-methyl)methylamino) propane), BES (N,N-bis(2-hydroxyethyl)-2-amino-ethanesulfonaic acid), MOPS (3-(N-morpholino) propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonicacid), MOBS (4-(N-morpholino) butanesulfonic acid), TAPSO (3-(N-tris (hydroxymethyl)methyl-amino)-2-hydroxypropanesulfonic acid), TRIZMA (tris(hydroxymethyl-aminomethane), HEPPSO(N-(2-hydroxyethyl)piperazine-N'-(2-hydroxy-propanesulfonic acid), POPSO (piperazine-N,N'-bis(2-hydroxypropane-sulfonic acid)), TEA (triethanolamine), EPPS(N-(2-hydroxyethyl)-piperazine-N'-(3-propanesulfonic acid), TRICINE (N-tris(hydroxy-methyl)methylglycine), GLY-GLY (glycylglycine), BICINE (N,N-bis(2-hydroxyethyl) glycine), HEPBS (N-(2-hydroxyethyl)piperazine-N'-(4-butanesulfonic acid)), TAPS(N-tris(hydroxymethyl)methyl-3-amino-propanesulfonic acid), AMPD (2-amino-2-methyl-1, 3-propanediol), and/or any other buffer known in the art.

Tonicity may, in addition to or in place of a buffering agent, be maintained using any pharmaceutically acceptable salt known in the art. Exemplary salts include sodium acetate, sodium lactate, sodium chloride, potassium chloride, and calcium chloride. Such salts, either along or in combination with the buffering agents, may be present in amount sufficient to maintain the desired tonicity (e.g., 1 mM, 10 mM, 20 mM, 50 mM, 100 mM, 200 mM, 500 mM, 1.0 M, 1.5 M, or any range between these values).

Other Excipients

In certain embodiments, the compositions and methods of the invention include other excipient such as a bulking agent or cryoprotectant). Bulking agents are particularly desirable where the pharmaceutical composition is provided in a dehydrated (e.g., lyophilized) form. Lyophilized compositions may contain less than 10% (e.g., less than 8%, 5%, 4%, 3%, 2%, 1%, 0.5%, 0.1%, 0.05%) water or other solvent by weight. Because dehydrated compositions administered by parenteral routes are typically dissolved in an aqueous solution prior to administration to a patient, it can be important that the dehydration process proceed in a manner allowing for resolubilization. Bulking agents can be added to ensure that the lyophilized product can be resolubilized more readily. Such agents are known in the art and include polyethylene glycol, polyvinyl alcohol, polyvinyl pyrrolidone, dextran; sugars such as dextrose, mannitol, sucrose, lactose, trehalose, and sorbitol; amino acids such as glycine, arginine, aspartic acid; and soluble proteins such as collagen, gelatin, or serum albumin.

The compositions may further comprise preservatives (e.g., thimerosal, benzyl alcohol, parabens), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially, and intratumorally.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the agent in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Methods of Treatment

The invention also features methods of treatment using the agents described herein. The anticancer agents and conjugates described herein (e.g., ANG1005) can be used to treat any cancer known in the art. Conjugates of the invention including the peptides described herein may be capable of crossing the BBB (e.g., AngioPep-1 through AngioPep-6) and thus may be used to treat any brain or central nervous system disease (e.g., a brain cancer such as glioblastoma, astrocytoma, glioma, meduloblastoma, and oligodendroma, neuroglioma, ependymoma, and meningioma). These conjugates may also be efficiently transported to the liver, lung, kidney, spleen or muscle (e.g., AngioPep-1 through AngioPep-7) and therefore may also be used, in conjunction with an appropriate therapeutic agent, to treat a disease associated with these tissues (e.g., a cancer such as hepatocellular carcinoma, liver cancer, small cell carcinoma (e.g., oat cell cancer), mixed small cell/large cell carcinoma, combined small cell carcinoma, and metastatic tumors. Metastatic tumors can originate from cancer of any tissue, including breast cancer, colon cancer, prostate cancer, sarcoma, bladder cancer, neuroblastoma, Wilm's tumor, lymphoma, non-Hodgkin's lymphoma, and certain T-cell lymphomas). Additional exemplary cancers that may be treated using a composition of the invention include hepatocellular carcinoma, breast cancer, cancers of the head and neck including various lymphomas such as mantle cell lymphoma, non-Hodgkins lymphoma, adenoma, squamous cell carcinoma, laryngeal carcinoma, cancers of the retina, cancers of the esophagus, multiple myeloma, ovarian cancer, uterine cancer, melanoma, colorectal cancer, bladder cancer, prostate cancer, lung cancer (including non-small cell lung carcinoma), pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease. Brain cancers that may be treated with vector that is transported efficiently across the BBB include astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, and teratoma.

A conjugate or composition of the invention may be administered by any means known in the art; e.g., orally, intraarterially, intranasally, intraperitoneally, intravenously, intramuscularly, subcutaneously, transdermally or per os to the subject. The agent may be, for example, an anti-angiogenic compound.

Dosages

The dosage of any conjugate or composition described herein or identified using the methods described herein depends on several factors, including: the administration method, the disease (e.g., cancer) to be treated, the severity of the disease, whether the cancer is to be treated or prevented, and the age, weight, and health of the subject to be treated.

With respect to the treatment methods of the invention, it is not intended that the administration of a vector, conjugate, or composition to a subject be limited to a particular mode of administration, dosage, or frequency of dosing; the invention contemplates all modes of administration. The conjugate, or composition may be administered to the subject in a single dose or in multiple doses. For example, a compound described herein or identified using screening methods of the invention may conjugate be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the composition. For example, the dosage of a composition can be increased if the lower dose does not provide sufficient activity in the treatment of a disease or condition described herein (e.g., cancer). Conversely, the dosage of the composition can be decreased if the disease (e.g., cancer) is reduced or eliminated.

While the attending physician ultimately will decide the appropriate amount and dosage regimen, a therapeutically effective amount of a vector, conjugate, or composition described herein, may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, every three weeks or once a month. Furthermore, a therapeutically effective amount of a compound may be, for example, in the range of 0.1 mg/m$^2$ to 2,000 mg/m$^2$ administered every other day, once weekly, every other week or every three weeks. For example ANG1005, may be administered at 50, 100, 200, 300, 400, 420, 500, 600, 700, 800, or 1,000 mg/m$^2$ every one, two, three, four weeks, or every month or every other month. In one particular example, ANG1005 is administered at 300 mg/m$^2$ or 420 mg/m$^2$ every three weeks. In another embodiment, the therapeutically effective amount is in the range of 1000 µg/m$^2$ to 20,000 µg/m$^2$, for example, at least 1000, 1500, 4000, or 14,000 µg/m$^2$ of the compound administered daily, every other day, twice weekly, weekly, or every other week.

The following examples are intended to illustrate rather than limit the invention.

Example 1

Solubility of ANG1005

The solubility of ANG1005 was tested in a number of solvents and surfactants. The results from single agents are shown in Table 13 below.

TABLE 13

ANG1005 solubilization
List of solvents/surfactants tested as single agents

| Solvents/surfactants | Solubility | Concentration |
|---|---|---|
| Acetonitrile (100%) | No | |
| EtOH dehydrated | No | |
| Methyl-tert-butyl-ether | No | |
| Acetone | No | |
| Ethyl acetate | No | |
| Tert-butyl alcohol | No | |
| N,N-Dimethylacetamide | Yes | 25 mg/ml |
| DMSO | Yes | 120 mg/ml |
| Polysorbate 80 (Tween 80) | No | |
| CREMOPHOR ® EL | No | |
| CREMOPHOR ® ELP (BASF) | No | |
| PEG 300 | No | |
| PEG | No | |
| PEG | No | |
| Polyvinylpyrrolidone (Kollidon 17) | No | |
| Polyvinylpyrrolidone (Kollidon 19) | No | |
| Cyclodextrin | No | |
| Labrafil | No | |

Solubility of ANG1005 was also tested in solvent/surfactant combinations. These results are shown in Table 14.

TABLE 14

ANG1005 solubilization
List of solvents/surfactants tested as combination

| Solvents/surfactants | Solubility | Concentration |
|---|---|---|
| EtOH/Tween 80 | No | |
| EtOH/CREMOPHOR ® EL | No | |
| EtOH/CREMOPHOR ® ELP | No | |
| EtOH/PEG | No | |
| EtOH/Polyvinylpyrrolidone | No | |
| SOLUTOL ® HS15/Buffer (with microwave heating) | Yes | 6 mg/ml |
| EtOH/SOLUTOL ® HS15/Buffer (75° C.) | Yes | 6 mg/ml |
| DMSO/SOLUTOL ® HS15/Buffer (50° C.) | Yes | 6 mg/ml |
| DMSO/Tween80/Buffer (65° C.) | Yes | 6 mg/ml |
| DMSO/CREMOPHOR ®/Buffer (65° C.) | Yes | 6 mg/ml |

Example 2

ANG1005 Solubilization Conditions

ANG1005 was subjected to several solubilization conditions in preparation for lyophilization. A summary of these results is shown below. As described above, the ANG1005 was dissolved first in DMSO. To this mixture, the heated SOLUTOL® or SOLUTOL® buffer combination was added. Finally, the glycine buffer was added to the ANG1005/DMSO/SOLUTOL® mixture. The solubilization conditions in Table 15 were thus tested.

50° C. The pH of the solution should be above 4.5 to enable the formation of micelles by the SOLUTOL® HS 15, as pH 4.5 reconstitution can result in turbid solutions. Acidification of the SOLUTOL® HS15 prior to adding ANG1005 minimizes its degradation.

Example 3

Lyophilization Conditions

Following dissolution, the ANG1005 mixture was diluted in aqueous buffer (e.g., glycine buffer, pH adjusted to 5.0 with HCl, mannitol, and sodium chloride), frozen and lyophilized. Exemplary conditions are described in Table 4 above.

Load temperatures from −70° C. to 25° C. were tested for segment one. The ramp time for segment 2 was varied according to the difference between the temperatures in segments 1 and 3, and may be up to six hours. We determined that segment 3 must be performed for at least 12 hours, as shorter timeframes resulted in a collapse of the lyophilized cake. Segments 8 and 9 can be adjusted within the temperatures shows above to ensure product temperature is between 18° C. to 21° C. during the secondary drying. The product should remain under 25° C. to avoid melting. Using the solubilization/lyophilization protocols described herein, we were able, in some cases, to generate a product with greater than 96% purity with less than 1% residual DMSO, as shown in Table 17.

TABLE 15

Solubilization of ANG1005

| Pilot | Target final pH | DMSO pH (5%) | SOLUTOL ® (20%) | Buffer pH (75%) | Heating temperature |
|---|---|---|---|---|---|
| 1 | 4.50 | 4.0 (±0.5) | No adjustment | 4.0 (±0.2) | 42° C. |
| 2 | 4.75 | 4.0 (±0.5) | No adjustment | 4.3 (±0.2) | 42° C. |
| 3 | 5.00 | 4.0 (±0.5) | No adjustment | 4.5 (±0.2) | 42° C. |
| 4 | 5.25 | 4.0 (±0.5) | No adjustment | 4.8 (±0.2) | 42° C. |
| 5 | 4.50 | 4.0 (±0.5) | No adjustment | 4.0 | 46° C. |
| 6 | 4.75 | 4.0 (±0.5) | No adjustment | 4.3 (±0.2) | 46° C. |
| 7 | 5.00 | 4.0 (±0.5) | No adjustment | 4.5 (±0.2) | 46° C. |
| 8 | 5.25 | 4.0 (±0.5) | No adjustment | 4.8 (±0.2) | 46° C. |
| 9 | 4.50 | 4.0 (±0.5) | No adjustment | 4.0 | 50° C. |
| 10 | 4.75 | 4.0 (±0.5) | No adjustment | 4.3 (±0.2) | 50° C. |
| 11 | 5.00 | 4.0 (±0.5) | No adjustment | 4.5 (±0.2) | 50° C. |
| 12 | 5.25 | 4.0 (±0.5) | No adjustment | 4.8 (±0.2) | 50° C. |

| Pilot | Target final pH | DMSO pH (5%) | SOLUTOL ®/buffer: 80/20 (25%) | Buffer pH (70%) | Heating temperature |
|---|---|---|---|---|---|
| 13 | 4.50 | 4.0 (±0.5) | pH = 5.0 (±0.5) | 5.0 (±0.2) | 50° C. |
| 14 | 4.75 | 4.0 (±0.5) | pH = 5.5 (±0.5) | 5.5 (±0.2) | 50° C. |
| 15 | 5.00 | 4.0 (±0.5) | pH = 6.0 (±0.5) | 5.5 (±0.2) | 50° C. |
| 16 | 5.25 | 4.0 (±0.5) | pH = 6.5 (±0.5) | 6.0 (±0.2) | 50° C. |

| Pilot | Target final pH | DMSO pH (5%) | SOLUTOL ®/water-HCl 80/20 (25%) | Buffer pH (70%) | Heating temperature |
|---|---|---|---|---|---|
| 17 | 5.00 | 4.0 (±0.5) | pH = 6.0 (±0.5) | 5.5 (±0.2) | 50° C. |

Results of these experiments are shown

TABLE 16

| Pilot | Target pH | Purity (%) | DMSO (ppm)* | Comments |
|---|---|---|---|---|
| 1 | 4.50 | 95.9 | 5855 | fast, clear reconst. then turbid |
| 2 | 4.75 | 94.0 | 6488 | fast, clear reconst. OK |
| 3 | 5.00 | 95.0 | 6256 | fast, clear reconst. OK |
| 4 | 5.25 | 95.4 | 6382 | fast, clear reconst. OK |
| 5 | 4.50 | 96.0 | 6818 | fast, clear reconst then turbid |
| 6 | 4.75 | 94.4 | 6330 | fast, clear reconst. OK |
| 7 | 5.00 | 94.6 | 6806 | fast, clear reconst. OK |
| 8 | 5.25 | 94.0 | 6930 | fast, clear reconst. OK |
| 9 | 4.50 | 95.2 | 6235 | fast, clear reconst. OK |
| 10 | 4.75 | 93.8 | 6932 | fast, clear reconst. OK |
| 11 | 5.00 | 95.1 | 6302 | fast, clear reconst. OK |
| 12 (ref.) | 5.25 | 93.9 | 7846 | fast, clear reconst. OK |
| 13 | 4.50 | 97.6 | 7035 | turbid reconst. (++) |
| 14 | 4.75 | 97.4 | 7071 | fast, clear rec. then turbid and precipitate |
| 15 | 5.00 | 95.4-94.3 | 6818 | fast, clear reconst. OK |
| 16 | 5.25 | 95.9-96.2 | 7155 | fast, clear reconst. OK |
| 17 | 5.00 | 96.5 | 6163 | turbid reconst. (++) |

On this basis of these results, we have determined that the formulation can be processed at temperatures between 40 and

TABLE 17

Key results for the GMP batch of ANG1005 for Injection

| | C0807121 | C0907124 | C1007135 |
|---|---|---|---|
| Purity | 93.3% | 90.9% | 96.5% |
| 2:1 conjugate | 4.6% | 6.4% | 2.2% |

TABLE 17-continued

Key results for the GMP batch of
ANG1005 for Injection

|  | C0807121 | C0907124 | C1007135 |
|---|---|---|---|
| Assay | 93.8% | 94.2% | 100.4% |
| Water | 0.2% | 0.1% | 0.05% |
| DMSO | 8.2% | 2.4% | 0.6% |

Further characterization of the 1007135 batch and other batches is shown in the Table 18 below.

TABLE 18

| | Lot Number | | | | |
|---|---|---|---|---|---|
| | C1007135 | C0108002 | C0308011 | C0608030 | C1108062 |
| Purity | 96.5% | 96.9% | 95.5% | 95.6% | 96.9% |
| 2:1 conjuguate | 2.2% | 1.4% | 2.0% | 2.7% | 2.3% |
| Assay | 100.4% | 97.2% | 100.7% | 102.6% | 105.7% |
| Total Related Substances | 3.5% | 3.1% | 5.0% | 4.4% | 3.1% |
| Unconjugated Angiopep-2 | ND | ND | ND | ND | ND |
| Unconjugated Paclitaxel | 0.9% | 0.6% | 1.0% | 0.7% | 0.5% |
| 1:1 Conjugate | ND | ND | ND | ND | ND |
| Unknown | 0.5% | 1.0% | 1.0% | 1.0% | 0.4% |
| Water Content | 0.05% | 0.04% | 0.05% | 0.12% | 0.03% |
| DMSO | 0.65% | 0.54% | 0.37% | 0.54% | 0.64% |

ND = not detected

Example 4

Resuspension of Lyophilized ANG1005

The follow procedure was developed to dissolve and suspend the ANG1005 lyophilized formulation in aqueous solution. The procedure outlined is appropriate for a single vial containing 120 mg ANG1005.

The ANG1005 vial was equilibrated at room temperature. The vial was then vented. With a 20 cc syringe fitted with an 18 G 1½" needle, 4 ml of anhydrous ethanol was slowly (i.e., over 30 seconds) injected down the side of the vial. The vial was then placed on a nutating mixer for 10 minutes, resulting in the ethanol slowly moistening the cake, thus providing a milky suspension.

The vial was then removed from the mixer and, with a 20-cc plastic syringe fitted to an 18 G 1.5" needle, 12 ml of lactated Ringer's with 5% dextrose was injected down the side of the vial. The vial was then placed on the nutating mixer for 5 minutes. The vial was then turned vial 180 degrees and then keep mixing on the nutating mixer for another 5 minutes. At this point, the suspension was clear with minimal foaming. The vial was then allowed to stand on the bench for five minutes before proceeding to the next step (e.g., dilution for injection, analysis).

Alternate diluents were also tested (Table 19). While use of these diluents resulted in a clear solution with complete dissolution, they resulted in greater ANG1005 degradation than the mixture of lactated Ringer with 5% dextrose and ethanol at room temperature.

TABLE 19

Alternative diluents for Resuspension:

| | Quantity | Conditions |
|---|---|---|
| Water for Injection | 16 ml | Warm to 40-50° C. |
| Water for Injection/Ethanol | 12 ml + 4 ml | RT |
| D5W | 16 ml | Warm to 40-50° C. |
| D5W/Ethanol | 12 ml + 4 ml | RT |
| Lactated Ringer-D5W | 16 ml | Warm to 40-50° C. |

Example 5

Testing of Additional Buffers and Bulking Agents

Further efforts were undertaken with the objectives of reducing the residual DMSO (0.5%) and shortening the lyophilization cycle (5 days).

We believe that the various excipients of the formulation (especially the glycine and the sodium chloride) resulted in reduced efficiency of DMSO removal during the secondary drying of the cycle. Formulations made without NaCl, glycine, mannitol, or water resulted in much lower DSMO content (on the order of 0.01%). Without mannitol however, the cake was waxy-like (mainly consisting of SOLUTOL®). These low DMSO formulations all failed re-constitution using ethanol and D5W/lactated ringer. In addition, when the glycine was not present, the pH was not controlled. This resulted in degradation of the ANG1005.

Thus, in a further test, mannitol was kept as a bulking agent, glycine was replaced by buffers including citric acid and lactic acid, and the sodium chloride was removed. These formulations, using a shorter lyophilization cycle, still resulted in cakes with residual DMSO at 0.05%. At this level of DMSO, the cake was not soluble. In an additional formulation, soy lecithin was used in place of mannitol. This resulted in a residual DMSO of 0.2%. At 0.2% residual DMSO, the cake was soluble in Ethanol and D5W/LR. Thus, we believe that a minimum of 0.2-0.4% DMSO may be necessary for the reconstitution of the vials and the further dilution into the infusion bag. The lyophilization time can be adjusted accordingly to allow for DMSO concentrations in this range.

The compositions used in these tests are detailed as follows (Tables 20-22).

TABLE 20

Pre-lyophylization composition

| % w/w | Supplier | F-37 | F-38 | F-39 | F-40 |
|---|---|---|---|---|---|
| ANG1005 | | 0.72 | 0.72 | 0.72 | 0.72 |
| SOLUTOL ® HS15 | | 24.92 | 24.88 | 24.83 | 24.88 |
| DMSO, USP | Gaylord | 13.39 | 13.36 | 13.32 | 13.36 |
| 1N HCl | | 0.311 | 0.311 | 0.306 | 0.311 |
| Citric acid | | 0.04 | | | |
| Lactic acid** | | | 0.21 | 0.42 | 0.21 |
| Mannitol | | 1.54 | 1.53 | 1.53 | |
| Soy lecithin | PL90G | | | | 1.53 |
| Water for injection | | 59.08 | 59.00 | 58.86 | 59.00 |
| Total | | 100.00 | 100.00 | 100.00 | 100.00 |

**85% in water
The SOLUTOL ®/API ratio is same as in the ANG batch record
The DMSO/HCl ratio is same as in the ANG batch record
Citric acid conc is selected to provide pH 5 (based F-34)
Lactic acid conc is calculated to provide pH 5 (F38) and lower (F39)
Mannitol conc in water is the same as in the ANG batch record
Soy lecithin is a "solublizing" bulking agent to replace mannitol

TABLE 21

Compounding table

| Mg/tube | Grade & Lot | F-37 | F-38 | F-39 | F-40 |
|---|---|---|---|---|---|
| ANG1005 | | 184 | 184 | 184 | 184 |
| SOLUTOL ® HS15 | | 6328 | 6328 | 6328 | 6328 |
| DMSO, USP | | 3399 | 3399 | 3395 | 3399 |
| 1N HCl | | 79 | 79 | 78 | 79 |
| Citric acid | | 10 | | | |
| Lactic acid** | | | 54 | 108 | 54 |
| Mannitol | | 390 | 390 | 390 | |
| Soy lecithin | | | | | 390 |
| Water for injection | | 15000 | 15000 | 15000 | 15000 |
| Total | | 25390 | 25434 | 25483 | 25434 |
| Total Dry wt | | 6991 | 7035 | 7088 | 7035 |

**85% in water

TABLE 22

Post lyophilization composition table

| % w/w | Supplier | F-37 | F-38 | F-39 | F-40 |
|---|---|---|---|---|---|
| ANG1005 | | 2.64 | 2.62 | 2.60 | 2.62 |
| SOLUTOL ® HS15 | | 90.65 | 89.95 | 89.28 | 89.95 |
| DMSO, USP | Gaylord | | | | |
| 1N HCl | | 1.13 | 1.12 | 1.10 | 1.12 |
| Citric acid | | 0.14 | | | |
| Lactic acid** | | | 0.77 | 1.52 | 0.77 |
| Mannitol | | 5.59 | 5.54 | 5.50 | |
| Soy lecithin | | | | | 5.54 |
| Water for injection | | | | | |
| Total | | 100.0 | 100.0 | 100.0 | 100.0 |

**85% in water

The compositions were prepared as follows: The DMSO/HCl stock was prepared by weighing out 0.5 g 1N HCl standard solution into a 50 ml Falcon tube. 21.5 g DMSO was added and mixed well to obtain the DMSO+1N HCl stock.

For each composition mannitol, SOLUTOL®, citric or lactic acid, and WFI were weighed out and placed into a 50 ml Falcon tube. The contents were mixed well to dissolve. The tubes were capped and heated to 51° C. ("buffer mixture"). Another 50 ml was used to weigh out ANG1005. The DMSO/HCl stock was then added and mixed well by vortex until the solution became clear. The heated buffer mixture was slowly added to the DMSO/ANG1005 mixture while vortexing. The mixtures was then cooled to RT. 1700-1730 mg of the solution was then placed into each vial. The solution was lyophilized as described herein. The compound was stored at −20° C.

The solutions were then test for their ability to reconstituted. To reconstitute the solutions, ethanol was added and mixed. Ringer's lactate solution was then added. Amounts are shown in Table 23.

TABLE 23

Reconstitution Volume

| wt per vial | Ref Product | F-37 to F-40 |
|---|---|---|
| API (mg) | 125 | 12.5 |
| Ethanol (mg) | 3234 | 323.4 |
| Ringer's lactate with D5W (mg) | 12186 | 1218.6 |

If reconstitution is successful, then the sample appearance was to be recorded (color, crystal or solid PPT under microscope etc.). An aliquot would then be analyzed by HPLC (e.g., assay and purity). pH would also be measured.

Example 6

Stability Testing of the Lyophilized ANG1005 Product

Stability testing over time of the ANG1005 product is being tested. The lyophilized product, which is being store at about −15° C., was monitored for activity, purity, appearance, pH, and degration. The results of these tests are shown in Table 24 below.

TABLE 24

Stability Results for ANG1005 for Injection,
Lot Number C1007135 Stored at −15 ± 5° C.

ANG1005 for Injection. Lot Number C1007135  Strength: 120 mg/vial of ANG1005
Date of Manufacture: October 2007  Stability Study Start Date: November 2007
Package: 60 ml vial, with a 15 mm Daikyo stopper  Length of Study: 24 months
and 15 mm flip-off seal

| Tests | Initial | 1 Month | 2 Months | 3 Months | 6 Months | 9 Months | 12 Months | 16 months |
|---|---|---|---|---|---|---|---|---|
| Appearance | Conforms | Conforms | Conforms | Conforms | Conforms | Conforms | Conforms | Conforms |
| Clarity and completeness of Solution | Conforms | Conforms | Conforms | Conforms | Conforms | Conforms | Conforms | Conforms |
| pH | 5.2 | 5.9 | 5.5 | 5.5 | 5.5 | 5.8 | 5.8 | 5.7 |
| Water Content | 0.1% | 0.1% | 0.1% | 0.1% | 0.1% | ND | ND | 0.1% |
| Assay (wt/wt) | 100.4% | 97.6% | 98.4% | 97.5% | 93.7% | 103.3% | 103.5% | 101.3% |
| Purity | 96.5% | 97.4% | 97.2% | 96.7% | 96.2% | 97.3% | 97.4% | 97.2% |
| 2:1 Conjuguate | 2.2% | 1.4% | 1.5% | 1.5% | 1.4% | 1.3% | 1.2% | 1.4% |
| Paclitaxel | 0.9% | 0.6% | 0.7% | 0.6% | 1.1% | 0.5% | 0.5% | 0.6% |

TABLE 24-continued

Stability Results for ANG1005 for Injection,
Lot Number C1007135 Stored at −15 ± 5° C.

| Unknown Rel Substances | 0.5% | 0.4% | 0.4% | 1.2% | 1.3% | 0.8% | 0.8% | 0.8% |
|---|---|---|---|---|---|---|---|---|
| Imp RRT 0.60 | ND | ND | ND | ND | ND | ND | ND | ND |
| Imp RRT 0.61 | ND | ND | ND | ND | ND | ND | ND | ND |
| Imp RRT 0.62 | ND | ND | ND | ND | ND | ND | ND | ND |
| Imp RRT 0.64 | ND | ND | ND | ND | ND | ND | ND | ND |
| Imp RRT 0.66 | ND | ND | ND | ND | ND | ND | ND | ND |
| Imp RRT 0.79 | ND | ND | ND | ND | ND | ND | ND | ND |
| Imp RRT 0.83 | 0.1% | ND | ND | ND | 0.1% | ND | ND | ND |
| Imp RRT 0.91 | ND | ND | ND | ND | ND | ND | ND | ND |
| Imp RRT 0.93 | 0.3% | 0.3% | 0.3% | 0.3% | 0.3% | 0.3% | 0.3% | 0.3% |
| Imp RRT 0.95 | ND | ND | ND | 0.1% | ND | ND | 0.1% | 0.1% |
| Imp RRT 0.98 | ND | ND | ND | 0.3% | 0.2% | ND | ND | 0.2% |
| Imp RRT 1.03 | ND | 0.2% | 0.2% | 0.2% | 0.1% | ND | ND | ND |
| Imp RRT 1.04 | 0.2% | ND | ND | ND | 0.2% | ND | 0.2% | 0.1% |
| Imp RRT 1.06 | 0.1% | 0.1% | 0.1% | 0.2% | 0.2% | 0.5% | 0.2% | 0.1% |
| Imp RRT 1.07 | 0.1% | 0.1% | ND | 0.2% | ND | ND | ND | ND |
| Sterility | Sterile Conforms | N/Ap | N/Ap | N/Ap | N/Ap | N/Ap | Sterile Conforms | N/Ap |
| Particulate Matter | Conforms | N/Ap | N/Ap | N/Ap | N/Ap | N/Ap | Conforms | N/Ap |

Example 7

Stability of the ANG1005 Product Following Reconstitution

Several experiments have been performed to evaluate the stability of ANG1005 following reconstitution into solution. These experiments are described below.

Experiment 1

Product from lot number C0108002 of ANG1005 for Injection was reconstituted as described herein to a concentration range of 1.0 to 2.0 mg/ml. The concentration of 2.0 mg/ml of ANG1005 was previously determined to be the highest feasible dose for clinical use as previously presented in the IND. These preliminary experiments were conducted in small volumes in glass vials. Samples were kept at room temperature and visually inspected at the various time-points. Selected samples were filtered prior to HPLC analysis.

Table 25 shows the visual clarity of the solutions across the concentrations tested over time. The appearance of cloudiness appears to correlate with both increasing concentration and time. HPLC analysis of selected samples revealed a single ANG1005 peak that did not significantly change in purity over the various time-points. No changes in the profile of the related substances were observed (Table 26). Two related substance peaks are noted and identified as the 2:1 conjugate (RRT 0.88) and unconjugated paclitaxel (RRT 0.95). A peak was observed with a RRT of 1.15 (8.1 minutes); this peak is an impurity from the HPLC column, as it is also present in the blank chromatograms.

TABLE 25

Visual appearance of reconstituted ANG1005 diluted in D5W

| | 0 h | 1 h | 2 h | 3 h | 4 h | 6 h |
|---|---|---|---|---|---|---|
| 1.0 mg/ml | Clear | Clear | Clear | Clear | Clear | X |
| 1.5 mg/ml | Clear | Clear | X | X | XX | XXX |
| 2.0 mg/ml | Clear | X | XX | XX | XXX | XXX |

X: Slightly cloudy
XX: Cloudy
XXX: Very cloudy

TABLE 26

Purity of reconstituted ANG1005 for Injection diluted in D5W

| | 0 h | 1.5 h | 3.5 h | 6 h |
|---|---|---|---|---|
| 1.0 mg/ml | 97.3% Related Substances: 1.3% (0.88) 1.4% (0.95) | NT | 97.1% Related Substances: 1.4% (0.88) 1.5% (0.95) | NT |
| 1.5 mg/ml | 97.3% Related Substances: 1.3% (0.88) 1.4% (0.95) | 97.1% Related Substances: 1.4% (0.88) 1.5% (0.95) | NT | 96.8% Related Substances: 1.5% (0.88) 1.7% (0.95) |
| 2.0 mg/ml | 97.2% Related Substances: | 97.1% Related Substances: | NT | NT |

TABLE 26-continued

Purity of reconstituted ANG1005 for Injection diluted in D5W

| 0 h | 1.5 h | 3.5 h | 6 h |
|---|---|---|---|
| | 1.3% (0.88) | 1.4% (0.88) | |
| | 1.5% (0.95) | 1.5% (0.95) | |

NT = Not tested
Related substances: report single peak greater than 0.5% with relative retention time in parentheses
Related substance at RRT 0.88 represents the 2:1 conjugate
Related substance at RRT 0.95 represents the unconjugated paclitaxel
Note:
A peak is observed with a relative retention time of 1.15 (8.1 min); this peak is an impurity from the HPLC column as it is also present in blank chromatogram.

Experiment 2

In order to verify the stability results at 1.0 mg/ml that was obtained in Experiment 1, an additional study was conducted under the conditions of clinical use. ANG1005 for Injection, lot number C0108002, was reconstituted as described to prepare a final concentration of 1.0 mg/ml in the 500 ml D5W infusion bag. The solution remained visually clear over the 6-hour observation period at room temperature with no significant changes in purity or related substance profiles (see Table 27 and FIG. 2).

TABLE 27

Purity of reconstituted ANG1005 for Injection diluted with D5W to 1.0 mg/ml under conditions of clinical use

| | Time | | | |
|---|---|---|---|---|
| | 0 h | 2 h | 4 h | 6 h |
| Purity | 97.4% | 97.3% | 97.0% | 97.2% |
| | Related Substances: | Related Substances: | Related Substances: | Related Substances: |
| | 1.2% (0.88) | 1.3% (0.88) | 1.5% (0.88) | 1.4% (0.88) |
| | 1.4% (0.95) | 1.4% (0.95) | 1.5% (0.95) | 1.4% (0.95) |

Related substances: report single peak greater than 0.5% with relative retention time in parentheses.
Related substance at RRT 0.88 represents the 2:1 conjugate
Related substance at RRT 0.95 represents the unconjugated paclitaxel
Note:
A peak is observed with a relative retention time of 1.15 (8.1 min); this peak is an impurity from the HPLC column as it is also present in blank chromatogram.

Experiment 3

Figure 3:
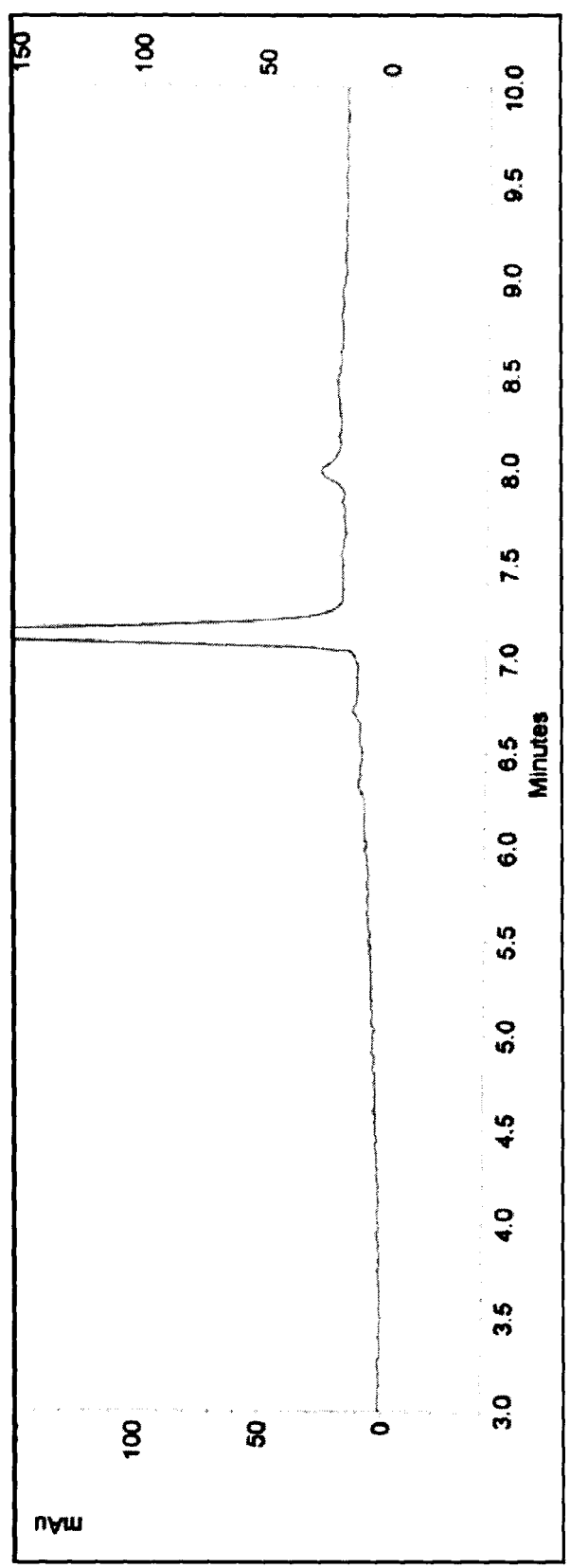
FIG. 3 is a graph showing the HPLC profile of the centrifuged sediment collected from the sample at 2.0 mg/mL and ~6 h storage, and solubilized in DMSO.

ANG1005 for Injection, lot number C0108002 was reconstituted and diluted in D5W to a final concentration of 2.0 mg/ml in a glass vial. The sample was kept at room temperature for ~6 h. The solution became cloudy and was centrifuged. The resulting sediment was collected by decanting the supernatant, was solubilized in DMSO, and was analyzed by HPLC. The main peak of the re-solubilized sediment was identified as ANG1005 with a purity of 97.2%. No change in the profile of related substances was observed and only the 2 expected additional peaks were present (1.3% at RRT 0.88 and 1.5% at RRT 0.95). The HPLC chromatogram of this sample is shown in FIG. 3. A peak is observed with a RRT of 1.15 (8.1 minutes); this peak is an impurity from the HPLC column and is also present in the blank chromatograms.

The collective data indicate that the turbidity/cloudiness observed is a result of intact ANG1005 going out of solution without any degradation, likely due to an interaction between the components of the drug product and D5W. This phenomenon appears to be concentration and time-dependent.

To reduce the turbidity, a reduction of the final concentration to <1 mg/ml for all patients receiving doses of ANG1005 >300 mg/m² was suggested.

There is some data to suggest that this finding is mostly due to the reduction of the amount of residual DMSO in the drug product. The first batch of drug product, lot number C0807121, had a residual DMSO content of 8.2%, whereas a more recent lot, lot number C0108002, has a residual DMSO content of 0.54%. It appears that this change may have affected the solubility of the substance.

Additional experiments are underway to modify the dilution procedure to increase the stability of the reconstituted drug. Solutions prepared with Lactated Ringer's instead of 5% Dextrose Injection as the diluent in the last step of the reconstitution process are being tested: each vial of ANG1005 for Injection will be first reconstituted with 4 ml of anhydrous ethanol and 12 ml of Lactated Ringer's/5% Dextrose Injection as before to achieve a concentration of 6 mg/ml, and then further diluted with Lactated Ringer's Injection. Preliminary data, shown in Table 28, suggest the replacement of D5W by Lactated Ringer's at the same concentration range (up to 2.0 mg/ml) can prevent the observed cloudiness of the infusion solutions. All solutions remained clear throughout the observation period without affecting the purity of ANG1005.

TABLE 28

Purity of reconstituted ANG1005 for Injection diluted with Lactated Ringer's Injection

| | 0 h | 1 h | 2 h | 4 h |
|---|---|---|---|---|
| 0.5 mg/ml | 97.2% | 96.9% | 96.7% | 96.3% |
| | Related Substances: | Related Substances: | Related Substances: | Related Substances: |
| | 1.4% (0.88) | 1.5% (0.88) | 1.7% (0.88) | 2.0% (0.88) |
| | 1.4% (0.95) | 1.6% (0.95) | 1.6% (0.95) | 1.7% (0.95) |
| 1.0 mg/ml | 96.8% | 96.7% | 96.6% | 96.6% |
| | Related Substances: | Related Substances: | Related Substances: | Related Substances: |
| | 1.6% (0.88) | 1.7% (0.88) | 1.8% (0.88) | 1.8% (0.88) |
| | 1.6% (0.95) | 1.6% (0.95) | 1.6% (0.95) | 1.6% (0.95) |
| 1.5 mg/ml | 97.0% | 96.9% | 96.6% | 96.6% |
| | Related Substances: | Related Substances: | Related Substances: | Related Substances: |
| | 1.5% (0.88) | 1.6% (0.88) | 1.8% (0.88) | 1.8% (0.88) |
| | 1.5% (0.95) | 1.5% (0.95) | 1.6% (0.95) | 1.6% (0.95) |
| 2.0 mg/ml | 97.1% | 96.8% | 96.6% | 96.6% |
| | Related Substances: | Related Substances: | Related Substances: | Related Substances: |
| | 1.4% (0.88) | 1.6% (0.88) | 1.8% (0.88) | 1.8% (0.88) |
| | 1.5% (0.95) | 1.6% (0.95) | 1.6% (0.95) | 1.6% (0.95) |

Related substances: report single peak greater than 0.5% with relative retention time in parentheses.
Related substance at RRT 0.88 represents the 2:1 conjugate
Related substance at RRT 0.95 represents the unconjugated paclitaxel Other Embodiments All patents, patent applications, and publications mentioned in this specification are herein incorporated by reference to the same extent as if each independent patent, patent application, or publication was specifically and individually indicated to be incorporated by reference.

What is claimed is:

1. A composition comprising:
   (a) a conjugate comprising:
      (i) a polypeptide comprising an amino acid sequence having at least 70% identity to AngioPep-1 (SEQ ID NO:67); AngioPep-2 (SEQ ID NO:97), or AngioPep-7 (SEQ ID NO:112); and
      (ii) a therapeutic agent selected from the group consisting of paclitaxel and a paclitaxel analog, wherein said therapeutic agent is conjugated to a polypeptide;
   (b) an optional tonicity agent;
   (c) a buffering agent, wherein said buffering agent maintains a pH of 4.5-6;
   (d) a bulking agent; and
   (e) a solubilizing agent, wherein said solubilizing agent is not ethoxylated castor oil;
   (f) 0.2 to 10% DMSO,
   wherein said paclitaxel analog is selected from the group consisting of ((azidophenyl)ureido)taxoid, (2α,5α,7β,9α,10β,13α)-5,10,13,20-tetraacetoxytax-11-ene-2,7,9-triol, (2α,5α,9α,10β)-2,9,10-triacetoxy-5-(((β-D-glucopyranosyl)oxy)-3,11-cyclotax-11-en-13-one, 1β-hydroxybaccatin I, 1,7-dihydroxytaxinine, 1-acetyl-5,7,10-deacetyl-baccatin I, 1-dehydroxybaccatin VI, 1-hydroxy-2-deacetoxy-5-decinnamoyl-taxinine j, 1-hydroxy-7,9-dideacetylbaccatin I, 1-hydroxybaccatin I, 10-acetyl-4-deacetyltaxotere, 10-deacetoxypaclitaxel, 10-Deacetyl baccatin III dimethyl sulfoxide disolvate, 10-deacetyl-10-(3-aminobenzoyl)paclitaxel, 10-deacetyl-10-(7-(diethylamino)coumarin-3-carbonyl)paclitaxel, 10-deacetyl-9-dihydrotaxol, 10-deacetylbaccatine III, 10-deacetylpaclitaxel, 10-deacetyltaxinine, 10-deacetyltaxol, 10-deoxy-10-C-morpholinoethyl docetaxel, 10-O-acetyl-2-O-(cyclohexylcarbonyl)-2-debenzoyltaxotere, 10-O-sec-aminoethyl docetaxel, 11-desmethyllaulimalide, 13-deoxo-13-acetyloxy-7,9-diacetyl-1,2-dideoxytaxine, 13-deoxybaccatin III, 14-hydroxy-10-deacetyl-2-O-debenzoylbacatin III, 14-hydroxy-10-deacetylbaccatin III, 14β-benzoyloxy-13-deacetylbaccatin IV, 14β-benzoyloxy-2-deacetylbaccatin VI, 14β-benzoyloxybaccatin IV, 19-hydroxybaccatin III, 2',2"-methylenedocetaxel, 2',2"-methylenepaclitaxel, 2'-(valyl-leucyl-lysyl-PABC)paclitaxel, 2'-acetyltaxol, 2'-O-acetyl-7-O—(N-(4'-fluoresceincarbonyl)alanyl)taxol, 2,10,13-triacetoxy-taxa-4(20),11-diene-5,7,9-triol, 2,20-O-diacetyltaxumairol N, 2-(4-azidobenzoyl)taxol, 2-deacetoxytaxinine J, 2-debenzoyl-2-m-methoxybenozyl-7-triethylsilyl-13-oxo-14-hydroxybaccatin III 1,14-carbonate, 2-O-(cyclohexylcarbonyl)-2-debenzoylbaccatin III 13-O—(N-(cyclohexylcarbonyl)-3-cyclohexylisoserinate), 2α,7β,9α,10β,13α-pentaacetoxyltaxa-4 (20), 11-dien-5-ol, 2α,5α,7β,9α,13α-pentahydroxy-10β-acetoxytaxa-4(20),11-diene, 2α,7β,9α,10β,13-pentaacetoxy-11β-hydroxy-5α-(3'-N,N-dimethylamino-3'-phenyl)-propionyloxytaxa-4(20),12-diene, 2α,7β-diacetoxy-5α,10β,13β-trihydroxy-2(3-20)abeotaxa-4(20),11-dien-9-one, 2α,9α-dihydroxy-10β,13α-diacetoxy-5α-(3'-methylamino-3'-phenyl)-propionyloxytaxa-4(20),11-diene, 2α-hydroxy-7β,9α,10β,13α-tetraacetoxy-5α-(2'-hydroxy-3'-N,N-dimethylamino-3'-phenyl)-propionyloxytaxa-4(20),11-diene, 3'-(4-azidobenzamido)taxol, 3'-N-(4-benzoyldihydrocinnamoyl)-3'-N-debenzoylpaclitaxel, 3'-N-m-aminobenzamido-3'-debenzamidopaclitaxel, 3'-p-hydroxypaclitaxel, 3,11-cyclotaxinine N,N-2,4-deacetyltaxol, 5,13-diacetoxy-taxa-4(20),11-diene-9,10-diol, 5-O-benzoylated taxinine K, 5-O-phenylpropionyloxytaxinine A, 5α,13α-diacetoxy-10β-cinnamoyloxy-4(20),11-taxadien-9α-ol, 6,3'-p-dihydroxypaclitaxel, 6-α-hydroxy-7-deoxy-10-deacetylbaccatin-III, 6-fluoro-10-acetyldocetaxel, 6-hydroxytaxol, 7,13-diacetoxy-5-cinnamyloxy-2(3-20)-abeo-taxa-4(20),11-diene-2,10-diol, 7,9-dideacetylbaccatin VI, 7-(5'-Biotinylamidopropanoyl)paclitaxel, 7-acetyltaxol, 7-deoxy-10-deacetylbaccatin-III, 7-deoxy-9-dihydropaclitaxel, 7-epipaclitaxel, 7-methylthiomethylpaclitaxel, 7-O-(4-benzoyldihydrocinnamoyl)paclitaxel, 7-O—(N-(4'-fluoresceincarbonyl)alanyl)taxol, 7-xylosyl-10-deacetyltaxol, 8,9-single-epoxy brevifolin, 9-dihydrobaccatin III, 9-dihydrotaxol, 9α-hydroxy-2α,10β,13α-triacetoxy-5α-(3'-N,N-dimethylamino-3'-phenyl)-propionyloxytaxa-4(20),11-diene, baccatin III, baccatin III 13-O—(N-benzoyl-3-cyclohexylisoserinate), BAY59, benzoyltaxol, BMS 181339, BMS 185660, BMS 188797, brevifoliol, butitaxel, cephalomannine, dantaxusin A, dantaxusin B, dantaxusin C, dantaxusin D, dibromo-10-deacetylcephalomannine, DJ927, docetaxel, Flutax 2, glutarylpaclitaxel 6-aminohexanol glucuronide, IDN 5109, IDN 5111, IDN 5127, IDN 5390, isolaulimalide, laulimalide, MST 997, N-(paclitaxel-2'-O-(2-amino)phenylpropionate)-O-(β-glucuronyl)carbamate, N-(paclitaxel-2'-O-3,3-dimethyl butanoate)-O-(β-glucuronyl) carbamate, N-debenzoyl-N-(3-(dimethylamino) benzoyl)paclitaxel, nonataxel, octreotide-conjugated paclitaxel, paclitaxel-transferrin, PNU 166945, polyethylene glycol)-conjugated paclitaxel-2'-glycinate, polyglutamic acid-paclitaxel, protax, protaxel, RPR 109881A, SB T-101187, SB T-1102, SB T-1213, SB T-1214, SB T-1250, SB T-12843, tasumatrol E, tasumatrol F, tasumatrol G, taxa-4(20),11(12)-dien-5-yl acetate, taxa-4(20),11(12)-diene-5-ol, taxane, taxchinin N, taxcultine, taxezopidine M, taxezopidine N, taxine, taxinine, taxinine A, taxinine M, taxinine NN-1, taxinine N,N-7, taxol C-7-xylose, taxol-sialyl conjugate, taxumairol A, taxumairol B, taxumairol G, taxumairol H, taxumairol I, taxumairol K, taxumairol M, taxumairol N, taxumairol 0, taxumairol U, taxumairol V, taxumairol W, taxumairol-X, taxumairol-Y, taxumairol-Z, taxusin, taxuspinanane A, taxuspinanane B, taxuspine C, taxuspine D, taxuspine F, taxuyunnanine C, taxuyunnanine S, taxuyunnanine T, taxuyunnanine U, taxuyunnanine V, tRA-96023, wallifoliol, 1-deoxypaclitaxel, 10-deacetoxy-7-deoxypaclitaxel, 10-O-deacetylpaclitaxel 10-monosuccinyl ester, 10-succinyl paclitaxel, 12b-acetyloxy-2a,3,4,4a,5,6,9,10,11,12,12a,12b-dodecahydro-4,11-dihydroxy-12-(2,5-dimethoxybenzyloxy)-4a,8,13,13-tetramethyl-5-oxo-7,11-methano-1H-cyclodeca(3,4)benz(1,2-b)oxet-943-(tert-butyloxycarbonyl)amino-2-hydroxy-5-methyl-4-hexaenoate, 130-nm albumin-bound paclitaxel, 2'-paclitaxel methyl 2-glucopyranosyl succinate, 3'-(4-azidophenyl)-3'-dephenylpaclitaxel, 4-fluoropaclitaxel, 6,6,8-trimethyl-4,4a,5,6,7,7a,8,9-octahydrocyclopenta (4,5)cyclohepta(1,2-c)-furan-4,8-diol 4-(N-acetyl-3-phenylisoserinate), 6,6,8-trimethyl-4,4a,5,6,7,7a,8,9-octahydrocyclopenta(4,5)cyclohepta(1,2-c)-furan-4,8-diol 4-(N-tert-butoxycarbonyl-3-phenylisoserinate), 7-(3-methyl-3-nitrosothiobutyryl)paclitaxel, 7-deoxypaclitaxel, 7-succinylpaclitaxel, A-Z-CINN 310, AI-850, albumin-bound paclitaxel, AZ 10992, isotaxel, MAC321, MBT-0206, NK105, Pacliex, paclitaxel poliglumex, paclitaxel-EC-1 conjugate, polilactofate, and TXD 258.

2. The composition of claim 1, wherein said therapeutic agent is paclitaxel.

3. The composition of claim 2, wherein said conjugate is ANG1005.

4. The composition of claim 1, wherein said tonicity agent is sodium chloride.

5. The composition of claim 1, wherein said buffering agent is glycine, citric acid, or lactic acid, or said bulking agent is mannitol or sorbitol.

6. The composition of claim 1, wherein said solubilizing agent is polyoxyethylene ester of a fatty acid.

7. The composition of claim 6, wherein said solubilizing agent is 12-Hydroxystearic acid-polyethylene glycol copolymer.

8. The composition of claim 1, wherein said composition is substantially free from ethoxylated castor oil or is free of ethoxylated castor oil.

9. The composition of claim 1, wherein said composition is dissolved in water.

10. A composition comprising:

| Compound | Percentage (by non-water weight) |
|---|---|
| ANG1005 | 0.1-5% |
| Tonicity agent | 1-15% |
| Buffering agent | 1-10% |
| Bulking agent | 0-15% |
| 12-Hydroxystearic acid-polyethylene glycol copolymer | 40-75% |
| DMSO | 0.2-10%. |

11. The composition of claim 10, wherein said tonicity agent is sodium chloride, said buffering agent is glycine, and said bulking agent is mannitol.

12. The composition of claim 10 comprising:

| Compound | Percentage (by non-water weight) |
|---|---|
| ANG1005 | 1.8-2.3% |
| Tonicity agent | 9-11% |
| Buffer | 4.5-6% |
| Bulking agent | 8-10% |
| 12-Hydroxystearic acid-polyethylene glycol copolymer | 69-75% |
| DMSO | 0.2-2%. |

13. A composition comprising

| Compound | Percentage (by non-water weight) |
|---|---|
| ANG1005 | 1.8-4.0% |
| Buffer | 0.1-6% |
| Bulking agent | 2-10% |
| 12-Hydroxystearic acid-polyethylene glycol copolymer | 80-95% |
| DMSO | 0.2-1%. |

14. The composition of claim 13, wherein said buffer is lactic acid or citric acid and said bulking agent is mannitol.

15. The composition of claim 13, comprising the following:

| Compound | Percentage (by non-water weight) |
|---|---|
| ANG1005 | 2.0-3.0% |
| Buffer | 0.5-6% |
| Bulking agent | 4-7% |
| 12-Hydroxystearic acid-polyethylene glycol copolymer | 85-95% |
| DMSO | 0.2-0.6%. |

16. A method of administering a composition of claim 1 to patient suffering from a cancer, said method comprising administering to said patient said composition in an amount sufficient to treat said cancer.

17. A sealed container containing the composition of claim 11.

18. A method for preparing a pharmaceutical composition of claim 1, said method comprising:
(a) dissolving said conjugate in DMSO to form a mixture;
(b) adding said solubilizing agent to the mixture of step (a);
(c) adding water and said buffering agent to said mixture;
(d) lyophilizing mixture of step (c); wherein said lyophilization results in a reduction of the amount of said DMSO that results in a final concentration of 0-2-10% DMSO, but does not substantially reduce the amount of said solubilizing agent, thereby preparing said composition.

19. The method of claim 18, wherein said solubilizing agent is a polyoxyethylene ester of a fatty acid.

20. The method of claim 19, wherein said polyoxyethylene ester of a fatty acid is 12-Hydroxystearic acid-polyethylene glycol copolymer.

21. The method of claim 18, wherein said polypeptide comprises the amino acid sequence of AngioPep-1 (SEQ ID NO:67), AngioPep-2 (SEQ ID NO:97), or AngioPep-7 (SEQ ID NO:112).

22. The method of claim 21, wherein said conjugate is ANG1005.

23. The method of claim 18, wherein said step (d) lyophilizing comprises:
(i) freezing said mixture;
(ii) drying said frozen product at a first temperature and pressure sufficient to remove at least a portion of said water; and
(iii) drying said product at a second temperature and pressure sufficient to remove at least a portion of said DMSO.

24. The method of claim 23, wherein said solubilizing agent is 12-Hydroxystearic acid-polyethylene glycol copolymer.

25. The method of claim 18, wherein the mixture of step (b) is filtered prior to step (c) lyophilizing or wherein said mixture is placed into a vial prior to step (c) lyophilizing.

26. A method for producing a pharmaceutical composition of claim 1, said method comprising the steps:
(a) dissolving in DMSO said conjugate, wherein the therapeutic agent of said conjugate is paclitaxel or docetaxel, thereby forming a mixture;
(b) adding 12-Hydroxystearic acid-polyethylene glycol copolymer to said mixture;
(c) adding water, said buffering agent, said bulking agent, and optionally said tonicity agent to said mixture; and
(d) lyophilizing said mixture under conditions which remove said water and said DMSO from said mixture, wherein said DMSO remains at a final concentration of 0.2-10%, thereby producing said composition.

27. The method of claim 26, wherein said 12-Hydroxystearic acid-polyethylene glycol copolymer is mixed with water, said buffering agent, said bulking agent, and optionally said tonicity agent prior to adding to said mixture, wherein said water, buffering agent, bulking agent, and optional tonicity agent are added in an amount which maintains solubility of said conjugate in said mixture.

28. The method of claim 27, or wherein said DMSO is acidified between pH 3.5 and 4.5 prior to said step (a) dissolving.

29. The method of claim 26, wherein said conjugate comprises AngioPep-2 (SEQ ID NO:97).

30. A sealed container containing the composition of claim 14.

31. The method of claim 29, wherein said conjugate is ANG1005.

* * * * *

UNITED STATES PATENT AND TRADEMARK OFFICE
CERTIFICATE OF CORRECTION

PATENT NO.        : 8,710,013 B2  
APPLICATION NO.   : 12/988269  
DATED             : April 29, 2014  
INVENTOR(S)       : Demeule et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 470 days.

Signed and Sealed this
Fifteenth Day of December, 2015

Michelle K. Lee
*Director of the United States Patent and Trademark Office*

SEQUENCE LISTING

<160> NUMBER OF SEQ ID NOS: 116

<210> SEQ ID NO 1
<211> LENGTH: 19
<212> TYPE: PRT
<213> ORGANISM: Artificial Sequence
<220> FEATURE:
<223> OTHER INFORMATION: Synthetic

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Synthetic

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be amidated

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Synthetic

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Synthetic

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19

```
<212> TYPE: PRT
<213> ORGANISM: Artificial Sequence
<220> FEATURE:
<223> OTHER INFORMATION: Synthetic

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Synthetic

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Synthetic

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Synthetic

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Synthetic
```

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Synthetic

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Synthetic

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Synthetic

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Synthetic

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Synthetic

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Synthetic

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19

```
<212> TYPE: PRT
<213> ORGANISM: Artificial Sequence
<220> FEATURE:
<223> OTHER INFORMATION: Synthetic

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Synthetic

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Synthetic

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Synthetic

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Synthetic
```

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Synthetic

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Synthetic

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Synthetic

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Synthetic

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Synthetic

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Synthetic

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Synthetic

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Synthetic

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Synthetic

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Synthetic

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19

```
<212> TYPE: PRT
<213> ORGANISM: Artificial Sequence
<220> FEATURE:
<223> OTHER INFORMATION: Synthetic

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Synthetic

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Synthetic

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Synthetic

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Synthetic
```

```
<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Synthetic

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: Synthetic

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Synthetic

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Synthetic

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Synthetic

<400> SEQUENCE: 53

Thr Phe Phe Tyr Gly Gly Cys Leu Gly Asn Gly Asn Asn Phe Val Arg
1               5                   10                  15
```

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Synthetic

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Synthetic

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Synthetic

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Synthetic

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Synthetic

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19

```
<212> TYPE: PRT
<213> ORGANISM: Artificial Sequence
<220> FEATURE:
<223> OTHER INFORMATION: Synthetic

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Synthetic

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Synthetic

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Synthetic

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Synthetic

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: Synthetic

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: Synthetic

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be amidated

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: Synthetic

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Synthetic
```

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Synthetic

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Synthetic

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be amidated

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Synthetic

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Synthetic

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Synthetic

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Synthetic

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Synthetic

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Synthetic

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Synthetic

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Synthetic

<400> SEQUENCE: 84

Thr Phe Phe Tyr Gly Cys Gly Arg Gly Lys Arg Asn Asn Phe Lys Thr
1               5                   10                  15

Glu Glu Tyr

```
<210> SEQ ID NO 85
<211> LENGTH: 19
<212> TYPE: PRT
<213> ORGANISM: Artificial Sequence
<220> FEATURE:
<223> OTHER INFORMATION: Synthetic

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Synthetic

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Synthetic

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Synthetic

<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Synthetic

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
```

<220> FEATURE:
<223> OTHER INFORMATION: Synthetic

<400> SEQUENCE: 90

Arg Phe Lys Tyr Gly Gly Cys Leu Gly Asn Lys Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be amidated

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Synthetic

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Synthetic

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Synthetic

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Synthetic

```
<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Synthetic

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Synthetic

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Synthetic

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Synthetic

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Synthetic

<400> SEQUENCE: 100
```

```
Arg Phe Lys Tyr Gly Gly Cys Leu Gly Asn Lys Asn Tyr Leu Arg
1               5                   10                  15

Leu Lys Tyr
```

<210> SEQ ID NO 101
<211> LENGTH: 19
<212> TYPE: PRT
<213> ORGANISM: Artificial Sequence
<220> FEATURE:
<223> OTHER INFORMATION: Synthetic

<400> SEQUENCE: 101

```
Thr Phe Phe Tyr Gly Gly Cys Arg Ala Lys Arg Asn Asn Phe Lys Arg
1               5                   10                  15

Ala Lys Tyr
```

<210> SEQ ID NO 102
<211> LENGTH: 35
<212> TYPE: PRT
<213> ORGANISM: Artificial Sequence
<220> FEATURE:
<223> OTHER INFORMATION: Synthetic

<400> SEQUENCE: 102

```
Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
                20                  25                  30

Gly Gly Ala
        35
```

<210> SEQ ID NO 103
<211> LENGTH: 24
<212> TYPE: PRT
<213> ORGANISM: Artificial Sequence
<220> FEATURE:
<223> OTHER INFORMATION: Synthetic

<400> SEQUENCE: 103

```
Tyr Gly Gly Cys Arg Ala Lys Arg Asn Asn Phe Lys Ser Ala Glu Asp
1               5                   10                  15

Cys Met Arg Thr Cys Gly Gly Ala
                20
```

<210> SEQ ID NO 104
<211> LENGTH: 22
<212> TYPE: PRT
<213> ORGANISM: Artificial Sequence
<220> FEATURE:
<223> OTHER INFORMATION: Synthetic

<400> SEQUENCE: 104

```
Gly Leu Cys Gln Thr Phe Val Tyr Gly Gly Cys Arg Ala Lys Arg Asn
1               5                   10                  15

Asn Phe Lys Ser Ala Glu
                20
```

<210> SEQ ID NO 105
<211> LENGTH: 20
<212> TYPE: PRT
<213> ORGANISM: Artificial Sequence
<220> FEATURE:
<223> OTHER INFORMATION: Synthetic

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: Synthetic

<400> SEQUENCE: 106
atgagaccag atttctgcct cgagccgccg tacactgggc cctgcaaagc tcgtatcatc      60
cgttacttct acaatgcaaa ggcaggcctg tgtcagacct cgtatacgg cggctgcaga     120 gctaagcgta acaacttcaa atccgcggaa gactgcatgc gtacttgcgg tggtgcttag    180

<210> SEQ ID NO 107
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be acetylated

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Synthetic

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: May be acetylated

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:

<223> OTHER INFORMATION: Synthetic
<220> FEATURE:
<221> NAME/KEY: MISC_FEATURE
<223> OTHER INFORMATION: May be acetylated

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Synthetic

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Synthetic

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Synthetic

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Synthetic

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:

```
<223> OTHER INFORMATION: Synthetic

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:
<223> OTHER INFORMATION: Sythetic

<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20
```